United States Patent
Bolger et al.

(10) Patent No.: US 7,521,448 B2
(45) Date of Patent: Apr. 21, 2009

(54) N-SUBSTITUTED BENZIMIDAZOLYL C-KIT INHIBITORS

(75) Inventors: Joshua Bolger, Farmingdale, NY (US); Arlindo L. Castelhano, Farmingdale, NY (US); Andrew Phillip Crew, Farmingdale, NY (US); Han-Qing Dong, Farmingdale, NY (US); Ayako Honda, Farmingdale, NY (US); Radoslaw Laufer, Farmingdale, NY (US); An-Hu Li, Farmingdale, NY (US); Kristen Mulvihill, Farmingdale, NY (US); Li Qiu, Farmingdale, NY (US); Colin Peter Sambrook Smith, Oxford (GB); Yingchaun Sun, Farmingdale, NY (US); Graham Michael Wynne, Oxford (GB); Tao Zhang, Farmingdale, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 432 days.

(21) Appl. No.: 10/921,414

(22) Filed: Aug. 16, 2004

(65) Prior Publication Data

US 2006/0189629 A1    Aug. 24, 2006

Related U.S. Application Data

(60) Provisional application No. 60/496,806, filed on Aug. 21, 2003.

(51) Int. Cl.
*A61K 31/5377* (2006.01)
*C07D 413/12* (2006.01)

(52) U.S. Cl. .................... 514/234.5; 544/139
(58) Field of Classification Search ................ 544/139; 514/234.5
See application file for complete search history.

(56) References Cited

U.S. PATENT DOCUMENTS

| | | | |
|---|---|---|---|
| 3,951,920 A | 4/1976 | Senoo | |
| 4,975,435 A | 12/1990 | Campbell | |
| 5,111,688 A | 5/1992 | Houghton | |
| 5,360,809 A | 11/1994 | Axelsson | |
| 5,563,143 A | 10/1996 | Cohan | |
| 5,688,809 A | 11/1997 | Macor | |
| 5,814,651 A | 9/1998 | Duplantier | |
| 5,972,980 A | 10/1999 | Cornicelli | |
| 5,990,146 A * | 11/1999 | Boschelli et al. | 514/394 |
| 6,001,866 A | 12/1999 | Cornicelli | |
| 6,087,380 A | 7/2000 | Hauel | |
| 6,162,804 A | 12/2000 | Bilodeau | |
| 6,218,388 B1 | 4/2001 | Boschelli | |
| 6,218,547 B1 | 4/2001 | Teuber | |
| 6,316,444 B1 | 11/2001 | Hunt | |
| 6,316,474 B1 | 11/2001 | McCauley | |
| 6,326,379 B1 | 12/2001 | Macor | |
| 6,329,380 B1 | 12/2001 | Parsons | |
| 6,329,383 B1 | 12/2001 | Hedgecock | |
| 6,348,032 B1 | 2/2002 | Sperl | |
| 6,348,474 B1 | 2/2002 | Kayakiri | |
| 6,414,008 B1 | 7/2002 | Hauel | |
| 6,444,617 B1 | 9/2002 | Takaishi | |
| 6,465,484 B1 | 10/2002 | Bilodeau | |
| 6,469,039 B1 | 10/2002 | Hauel | |
| 6,479,508 B1 | 11/2002 | Beaulieu | |
| 6,498,165 B1 | 12/2002 | Armstrong | |
| 6,512,000 B1 | 1/2003 | Anderskewitz | |
| 6,534,535 B1 | 3/2003 | Zhu | |
| 6,548,524 B2 | 4/2003 | Levin | |
| 6,583,169 B2 | 6/2003 | Horvath | |
| 6,608,082 B1 | 8/2003 | Basu | |
| 7,019,147 B1 | 3/2006 | Barth | |
| 7,067,662 B2 | 6/2006 | Medina | |
| 7,329,684 B2 | 2/2008 | Mjalli | |
| 2002/0019395 A1 | 2/2002 | Bing-Yan | |
| 2002/0072530 A1 | 6/2002 | Zhu | |
| 2002/0128232 A1 | 9/2002 | Henderson | |
| 2003/0109714 A1 | 6/2003 | Wishart | |
| 2004/0224955 A1 | 11/2004 | Beaulieu | |
| 2006/0074119 A1 | 4/2006 | Andrews, III | |
| 2007/0161635 A1 | 7/2007 | Burns | |

FOREIGN PATENT DOCUMENTS

| | | |
|---|---|---|
| EP | 0846689 | 1/2004 |
| EP | 1085372 | 12/2004 |
| WO | WO 00/76501 | 12/2000 |
| WO | WO 02/59118 | 1/2001 |
| WO | WO 02/050057 | 10/2002 |

OTHER PUBLICATIONS

Van Craynest N et al., "Efficient synthesis of extended guanine analogues designed for recognition of an A. T. inverted base pair in triple helix based-strategy", Tetrahedron Letters, vol. 45, No. 33, Aug. 9, 2004, pp. 6243-6247, Elsevier Science Publishers, Amsterdam, NL.
International Search Report in PCT/US2004/026482.
International Preliminary Report on Patentability in PCT/US2004/026482.
Written Opinion of the International Search Authority in PCT/US2004/026482.

* cited by examiner

*Primary Examiner*—Patricia L Morris

(57) ABSTRACT

Compounds represented by Formula (I):

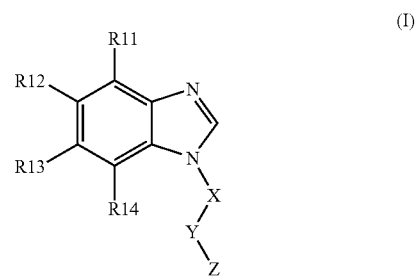

or a pharmaceutically acceptable salt or N-oxide thereof, are useful in the treatment of cancer.

6 Claims, No Drawings

N-SUBSTITUTED BENZIMIDAZOLYL C-KIT INHIBITORS

Applicants claim the benefit of U.S. Provisional Patent Application No. 60/496,806 filed Aug. 21, 2003.

BACKGROUND OF THE INVENTION

The present invention is directed to N-substituted benzimidazolyl compounds. In particular, the present invention is directed to N-substituted benzimidazolyl compounds that are inhibitors of the c-Kit proto-oncogene (also known as KIT, CD-117, stem cell factor receptor, mast cell growth factor receptor). The present invention is also directed to (N1-substituted) benzimidazolyl compounds that are inhibitors of c-Kit.

The c-Kit proto-oncogene is believed to be important in embryogenesis, melanogenesis, hematopoiesis, and the pathogenesis of mastocytosis, gastrointestinal tumors, and other solid tumors, as well as certain leukemias, including AML. Accordingly, it would be desirable to develop novel compounds that are inhibitors of the c-Kit receptor.

Many of the current treatment regimes for hyperproliferative disorders (cancer) utilize compounds that inhibit DNA synthesis. Such compounds' mechanism of operation is to be toxic to cells, particularly to rapidly dividing tumor cells. Thus, their broad toxicity can be a problem to the subject patient. However, other approaches to anti-cancer agents that act other than by the inhibition of DNA synthesis have been explored to try to enhance the selectivity of the anti-cancer action and thereby reduce adverse side-effects.

It is known that a cell may become cancerous by virtue of the transformation of a portion of its DNA into an oncogene (i.e. a gene which, on activation, leads to the formation of malignant tumor cells). Many oncogenes encode proteins that are aberrant protein-tyrosine kinases capable of causing cell transformation. By a different route, the overexpression of a normal proto-oncogenic tyrosine kinase can also result in proliferative disorders, sometimes resulting in a malignant phenotype. Alternatively, co-expression of a receptor tyrosine kinase and its cognate ligand within the same cell type may also lead to malignant transformation.

Receptor tyrosine kinases are large enzymes which span the cell membrane and possess i) an extracellular binding domain for growth factors such as KIT ligand (also known as stem cell factor (SCF), Steel factor (SLF) or mast cell growth factor (MGF)), ii) a transmembrane domain, and iii) an intracellular portion which functions as a kinase to phosphorylate specific tyrosine residues in proteins. Binding of KIT ligand to KIT tyrosine kinase results in receptor homodimerization, the activation of KIT tyrosine kinase activity, and the subsequent phosphorylation of a variety of protein substrates, many of which are effectors of intracellular signal transduction, These events can lead to enhanced cell proliferation or promote enhanced cell survival. With some receptor kinases, receptor heterodimerization can also occur.

It is known that such kinases are frequently aberrantly expressed in common human cancers such as breast cancer, head and neck cancers, gastrointestinal cancer such as colon, rectal or stomach cancer, leukemia, and ovarian, bronchial, lung or pancreatic cancer. KIT kinase expression has been documented in a wide variety of human malignancies such as mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma. The kinase activity of KIT has been implicated in the pathophysiology of several of these—and additional tumors—including breast carcinoma, SCLC, GIST, germ cell tumors, mast cell leukemia, neuroblastoma, AML, melanoma and ovarian carcinoma.

Several mechanisms of KIT activation in tumor cells have been reported, including activating mutations, autocrine and paracrine activation of the receptor kinase by its ligand, loss of protein-tyrosine phosphatase activity, and cross activation by other kinases. The transforming mechanisms initiated by the activating mutations are thought to include dimer formation and increased intrinsic activity of the kinase domain, both of which result in constitutive ligand-independent kinase activation, and possibly altered substrate specificity. More than thirty activating mutations of the Kit protein have been associated with highly malignant tumors in humans.

Accordingly, it has been recognized that inhibitors of receptor tyrosine kinases are useful as selective inhibitors of the growth of mammalian cancer cells. For example, Gleevec™ (also known as imatinib mesylate, or STI571), a 2-phenylpyrimidine tyrosine kinase inhibitor that inhibits the kinase activity of the BCR-ABL fusion gene product, was recently approved by the U.S. Food and Drug Administration for the treatment of CML. Gleevec™, in addition to inhibiting BCR-ABL kinase, also inhibits the KIT kinase and PDGF receptor kinase, although it is not effective against all mutant isoforms of the KIT kinase. Kit ligand-stimulated growth of MO7e human leukemia cells is inhibited by Gleevec™, which also induces apoptosis under these conditions. By contrast, GM-CSF stimulated growth of MO7e human leukemia cells is not affected by Gleevec™. Further, in recent clinical studies using Gleevec™ to treat patients with GIST, a disease in which KIT kinase is involved in transformation of the cells, many of the patients showed marked improvement.

These studies demonstrate how KIT kinase inhibitors can treat tumors whose growth is dependent on KIT kinase activity. Other kinase inhibitors show even greater kinase selectivity. For example, the 4-anilinoquinazoline compound Tarceva™ inhibits only EGF receptor kinase with high potency, although it can inhibit the signal transduction of other receptor kinases, probably by virtue of the fact that these receptors heterodimerize with EGF receptor.

Although anti-cancer compounds such as those described above make a significant contribution to the art, there is a continuing need for improved anti-cancer pharmaceuticals, and it would be desirable to develop new compounds with better selectivity or potency, or with reduced toxicity or side effects.

U.S. Pat. Nos. 5,990,146 and 6,218,388 describe benzimidazoles for inhibiting protein tyrosine kinase mediated cellular proliferation. U.S. Pat. No. 6,348,032 describes method of inhibiting neoplastic cells with benzimidazole derivatives. International Patent Publication No. WO 01/21634 describes benzimidazole derivatives and combinatorial libraries thereof. International Patent Publication No. WO 01/57020 describes indole and benzimidazole inhibitors of factor Xa. International Patent Publication No. WO 00/15222 describes fused pyridine inhibitors of cGMP phosphodiesterase. International Patent Publication No. WO 01/12600 describes inhibitors of Factor Xa. International Patent Publication No. WO 97/12613 describes method for treating and preventing inflammation and atherosclerosis.

U.S. Pat. No. 6,316,474 describes 2-benzyl and 2-heteroaryl benzimidazole NMDA/NR2b antagonists. U.S. Pat. No. 6,479,508 describes viral polymerase inhibitors. U.S. Pat. No. 6,444,617 describes fused-heterocycle dicarboxylic acid diamide derivatives or salts thereof, herbicide and usage thereof. U.S. Pat. Nos. 6,087,380, 6,414,008, and 6,469,039 describe disubstituted bicyclic heterocycles. U.S. Pat. No. 5,118,688 describes tetrahydropyridonquinolone derivatives. U.S. Pat. No. 4,975,435 describes certain 1H-pyrrolo[3,4-b]quinolin-1-one-9-amino-2,3-dihydro derivatives useful for treating anxiety. U.S. Pat. No. 6,548,524 describes ortho-sulfonamido bicyclic heteroaryl hydroxamic acids. U.S. Pat. No. 6,348,474 describes sulfonamide compounds.

U.S. Pat. Nos. 5,972,980 and 6,001,866 describe method for treating and preventing inflammation and atherosclerosis. U.S. Pat. No. 5,814,651 describes catechol diethers as selective PDEIV inhibitors. U.S. Pat. No. 6,329,383 describes 2-amino-5-pyrimidine acetic acid compounds. U.S. Pat. No. 5,688,809 describes 5-heteroarylindole derivatives. European Patent Application No. EP 0 846 689 describes benzimidazole compounds. International Patent Publication No. WO 00/59888 describes N-benzimidazolylmethyl- and N-indolylmethyl-benzamides and their use as CRF modulators. International Patent Publication No. WO 02/069965 describes benzimidazole derivatives as therapeutic agents. International Patent Publication No. WO 02/30886 describes heterocyclic angiogenesis inhibitors. U.S. Pat. No. 6,162,804 describes tyrosine kinase inhibitors. U.S. Pat. No. 6,465,484 describes angiogenesis inhibitors. International Patent Publication No. WO 00/12089 describes novel angiogenesis inhibitors.

German Patent Publication No. DE 2244908 describes selectively permeable polymeric membranes. European Patent Application No. EP 0 706 795 describes catechol diether compounds as inhibitors of TNF release. International Patent Publication No. WO 02/076960 describes transition metal mediated process. International Patent Publication No. WO 02/059118 describes process for N-(oxyalkylation) of carboxamides. International Patent Publication No. WO 02/04425 describes viral polymerase inhibitors. International Patent Publication No. WO 02/083143 describes CXCR3 antagonists. International Patent Publication No. WO 01/57019 describes indolone and benzimidazolone inhibitors of factor Xa. European Patent Application No. EP 1 085 372 describes photographic material having improved color reproduction. International Patent Publication No. WO 01/14342 describes aminocarbonyl-substituted benzimidazole derivatives. International Patent Publication No. WO 00/76501 describes IL-8 receptor antagonists.

Thus, it is desirable to develop compounds that exhibit Kit inhibition in order to treat oncology. Further, such compounds may be active in other kinases such as, for example, GIST, FLT3, Hematopoietic R-PTKs, PDGFR-beta or KDR to add efficacy in mast cell leukemias, small cell lung cancer (SCLC), mastocytosis, leukemias, myelodysplastic disorders, or angiogenic dependent diseases.

SUMMARY OF THE INVENTION

Compounds represented by Formula (I):

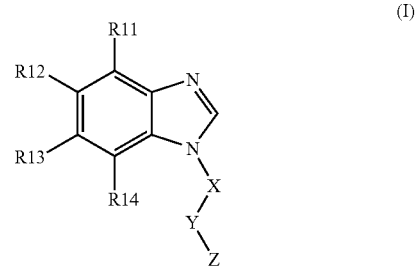

or a pharmaceutically acceptable salt or N-oxide thereof, are useful in the treatment of tumors.

DETAILED DESCRIPTION OF THE INVENTION

The present invention is directed to a compound represented by Formula (I):

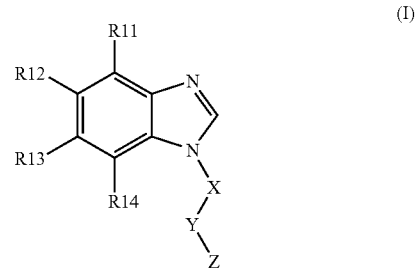

or a pharmaceutically acceptable salt or N-oxide thereof, wherein:

one of R11, R12, R13 and R14 is —NR$_3$COR$_{31}$, —NR$_3$CONR$_3$R$_{31}$, —NR$_3$SO$_2$R$_{31}$, —CO$_2$R$_3$, —CO$_2$H, —C$_{0-8}$alkylNR$_3$R$_{31}$ or —CONR$_3$R$_{31}$; the others each independently F, Cl, C$_{0-3}$alkyl, C$_{0-8}$alkoxy, or —N(C$_{0-8}$alkyl)(C$_{0-8}$alkyl);

X is a cyclyl or heterocyclyl group, optionally substituted with 1-4 halogen, —NR$_{32}$R$_{33}$, —NR$_{32}$COR$_{33}$, —NR$_{32}$CO$_2$R$_{33}$, —NR$_{32}$SO$_2$R$_{33}$, —OR$_{32}$, —SR$_{32}$, —SO$_2$R$_{32}$, —SO$_2$NR$_{32}$R$_{33}$, —CO$_2$R$_{32}$, —CO$_2$H, —CONR$_{32}$R$_{33}$, —C$_{0-8}$alkyl, —C$_{2-8}$alkenyl, —C$_{2-8}$alkynyl, —CN, CF$_3$, OCF$_3$, NO$_2$, oxo, cyclyl or heterocyclyl substituents;

Y is absent or

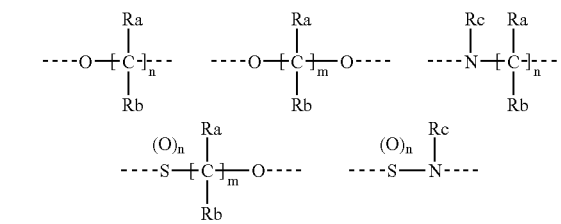

-continued

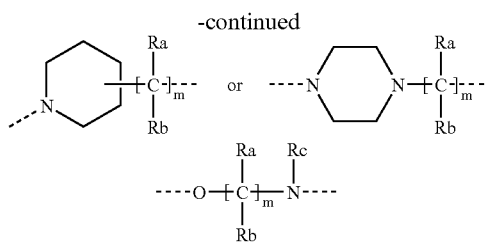

wherein the point of attachment to X can be from either the left or the right as shown;

$R_a$ and $R_b$ are each independently $C_{0-8}$alkyl or $C_{3-8}$cycloalkyl;

or $R_a$ and $R_b$ taken together with the C to which they are attached form a saturated or partially unsaturated 3-10 membered ring optionally containing 0-4 N, O, S, SO, or $SO_2$ at the ring nodes, provided that no N, O or S atoms are placed adjacent to each other at ring nodes;

Rc is $C_{0-8}$alkyl;

or Rc, taken with either $R_a$ or $R_b$, form a 3-7 membered saturated or partially unsaturated ring;

m is 0, 1, 2, 3, 4 or 5; provided that when m is 0 or 1, no N, O or S atoms are adjacent to each other in the N—X—Y-Z linking bridge;

n is 1, 2, 3, 4 or 5; provided that, when n is 1, no N, O or S atoms are adjacent to each other in the N—X—Y-Z linking bridge;

Z is a cyclyl or heterocycyl group, optionally substituted with 1-5 independent halogen, —$NR_{34}R_{35}$, —$NR_{34}COR_{35}$, —$NR_{34}C(O)OR_{35}$, —$NR_{34}SO_2R_{35}$, —$OR_{34}$, —$SR_{34}$, —$SO_2R_{34}$, —$SO_2NR_{34}R_{35}$, —$C(O)OR_{34}$, —$CO_2H$, —$CONR_{34}R_{35}$, $C_{0-8}$alkyl, $C_{2-8}$alkenyl, $C_{2-8}$alkynyl, —$OC_{0-8}$ alkyl, —$SC_{0-8}$alkyl, —$SO_2C_{0-8}$alkyl, —$SO_2N(C_{0-8}$alkyl)($C_{0-8}$alkyl), —$C(O)OC_{0-8}$alkyl, CN, $CF_3$, $NO_2$, oxo, cyclyl or heterocyclyl substituents; or, when Y is present, Z further can be $C_{0-8}$alkyl-O—$C_{0-8}$alkyl, $C_{0-8}$alkyl-O—C(O)—$C_{0-8}$alkyl, or $C_{0-8}$alkyl-C(O)—O—$C_{0-8}$alkyl;

provided that when Y is —$OCH_2$—, Z must be substituted with 1-5—$NR_{34}R_{35}$, —$NR_{34}COR_{35}$, —$NR_{34}C(O)OR_{35}$, —$NR_{34}SO_2R_{35}$, —$OR_{34}$, —$SR_{34}$, —$SO_2R_{34}$, —$SO_2NR_{34}R_{35}$, —$CO_2R_{34}$, —$CO_2H$, —$CONR_{34}R_{35}$, $C_{0-8}$alkyl, $C_{2-8}$alkenyl, $C_{2-8}$alkynyl, $CF_3$, $NO_2$, oxo, cyclyl or heterocyclyl substituents;

provided that when Y is $NHCH_2$, Z must be substituted with 1-5 halogen, —$NR_{34}R_{35}$, —$NR_{34}COR_{35}$, —$NR_{34}C(O)OR_{35}$, —$NR_{34}SO_2R_{35}$, —$OR_{34}$, —$SR_{34}$, —$SO_2R_{34}$, —$SO_2NR_{34}R_{35}$, —$CO_2R_{34}$, —$CO_2H$, —$CONR_{34}R_{35}$, $C_{0-8}$alkyl, $C_{2-8}$alkenyl, $C_{2-8}$alkynyl, $CF_3$, $NO_2$, oxo, cyclyl or heterocyclyl substituents;

provided that when Y is absent, X and Z cannot contain N;

$R_3$, $R_{31}$, $R_{32}$, $R_{33}$, $R_{34}$ and $R_{35}$ are independently $C_{0-8}$alkyl substituted with heterocyclyl, or OH substituents; $CF_3$, $CHF_2$, —$C_{0-8}$alkyl-O—$C_{0-8}$alkyl, —$C_{0-8}$alkyl-N($C_{0-8}$alkyl)($C_{0-8}$alkyl), —$C_{0-8}$alkyl-S(O)$_{0-2}$—$C_{0-8}$alkyl or —$C_{0-8}$alkyl-S(O)$_2$N($C_{0-8}$alkyl)($C_{0-8}$alkyl).

In one aspect, the present invention is directed to a compound represented by Formula (I), or a pharmaceutically acceptable salt or N-oxide thereof, wherein R12 is —$NR_3COR_{31}$, —$NR_3CONR_3R_{31}$, —$NR_3SO_2R_{31}$, —$CO_2R_3$, —$CO_2H$, —$C_{0-8}$alkyl$NR_3R_{31}$ or —$CONR_3R_{31}$; and the other variables are as described above for Formula (I).

In another aspect, the present invention is directed to a compound represented by Formula (I), or a pharmaceutically acceptable salt or N-oxide thereof, wherein R12 is —$CONR_3R_{31}$; and the other variables are as described above for Formula (I).

In an embodiment, the present invention is directed to a compound represented by Formula (I), or a pharmaceutically acceptable salt or N-oxide thereof, wherein R12 is —$CONR_3R_{31}$; X is cyclyl; and the other variables are as described above for Formula (I).

In another embodiment, the present invention is directed to a compound represented by Formula (I), or a pharmaceutically acceptable salt or N-oxide thereof, wherein R12 is —$CONR_3R_{31}$; X is heterocyclyl; and the other variables are as described above for Formula (I).

In still another embodiment, the present invention is directed to a compound represented by Formula (I), or a pharmaceutically acceptable salt or N-oxide thereof, wherein R12 is —$CONR_3R_{31}$; X is cyclyl; Y is absent; and the other variables are as described above for Formula (I).

In yet another embodiment, the present invention is directed to a compound represented by Formula (I), or a pharmaceutically acceptable salt or N-oxide thereof, wherein R12 is —$CONR_3R_{31}$; X is cyclyl; Y is

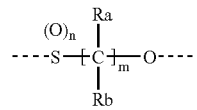

and the other variables are as described above for Formula (I).

In yet another embodiment, the present invention is directed to a compound represented by Formula (I), or a pharmaceutically acceptable salt or N-oxide thereof, wherein R12 is —$CONR_3R_{31}$; X is cyclyl; Y is

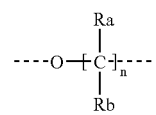

and the other variables are as described above for Formula (I).

In yet another embodiment, the present invention is directed to a compound represented by Formula (I), or a pharmaceutically acceptable salt or N-oxide thereof, wherein R12 is —$CONR_3R_{31}$; X is cyclyl; Y is

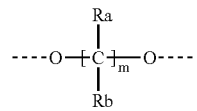

and the other variables are as described above for Formula (I).).

In yet another embodiment, the present invention is directed to a compound represented by Formula (I), or a pharmaceutically acceptable salt or N-oxide thereof, wherein R12 is —$CONR_3R_{31}$; X is cyclyl; Y is

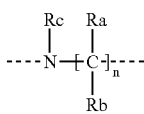

and the other variables are as described above for Formula (I).

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl", "carbocyclic ring", "cyclic", or "cyclyl" mean 3-10 membered mono or polycyclic aromatic, partially aromatic or non-aromatic ring carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$cycloalkyl such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "carbamoyl" unless specifically described otherwise means —C(O)—NH— or —NH—C(O)—.

The term "aryl" is well known to chemists. The preferred aryl groups are phenyl and naphthyl.

The term "hetaryl" is well known to chemists. The term includes 5- or 6-membered heteroaryl rings containing 1-4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like.

Unless otherwise stated, the terms "heterocyclic ring", "heterocycle", "heterocyclic", and "heterocyclyl" are equivalent, and is defined as for cyclic but also contains one or more atoms chosen independently from N, O, and S (and the N and S oxides), provided such derivatives exhibit appropriate and stable valencies and excludes moieties containing O—O, $S(O)_n$—$S(O)_n$, $S(O)_n$—O bonds where n=0-2. The terms include 4-8-membered saturated rings containing one or two heteroatoms chosen from oxygen, sulfur, and nitrogen. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, azepane, azocane, [1,3]dioxane, oxazolidine, piperazine, homopiperazine, morpholine, thiomorpholine, and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems, including het-het fused systems, and can include a carbocyclic ring that is partially or fully unsaturated, such as a benzene ring, to form benzofused heterocycles. For example, 3,4, -dihydro-1,4-benzodioxine, tetrahydroquinoline, tetrahydroisoquinoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably, the composition is comprised of a pharmaceutically acceptable carrier and a non-toxic therapeutically effective amount of a compound of Formula I as described above (or a pharmaceutically acceptable salt or N-oxide thereof).

Moreover, within this preferred embodiment, the invention encompasses a pharmaceutical composition for the treatment of disease by the inhibition of the c-Kit kinase, which may be a wild-type or mutant form of the protein, comprising a pharmaceutically acceptable carrier and a non-toxic therapeutically effective amount of compound of Formula I as described above (or a pharmaceutically acceptable salt or N-oxide thereof).

The compounds and compositions of the present invention are effective for treating mammals such as, for example, humans.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrochloric, maleic, phosphoric, sulfuric, methanesulfonic, and tartaric acids.

The pharmaceutical compositions of the present invention comprise a compound represented by formula I (or a pharmaceutically acceptable salt or N-oxide thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts or N-oxides thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt or N-oxide thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt or N-oxide of Formula I. The compounds of Formula I, or pharmaceutically acceptable salts or N-oxides thereof, can also be included in pharmaceutical compositions in combination with one or more other therapeutically active compounds.

The pharmaceutical compositions of this invention include a pharmaceutically acceptable liposomal formulation containing a compound of Formula I or a pharmaceutically acceptable salt or N-oxide thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt or N-oxide thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts or N-oxides thereof, may also be prepared in powder or liquid concentrate form.

Generally, dosage levels on the order of from about 0.01 mg/kg to about 750 mg/kg of body weight per day are useful in the treatment of the above-indicated conditions, or alternatively about 0.5 mg to about 75 g per patient per day. For example, breast cancer, head and neck cancers, and gastrointestinal cancer such as colon, rectal or stomach cancer may be effectively treated by the administration of from about 0.01 to 500 mg of the compound per kilogram of body weight per day, or alternatively about 0.5 mg to about 50 g per patient per day.

Similarly, leukemia, ovarian, bronchial, lung, and pancreatic cancer may be effectively treated by the administration of from about 0.01 to 500 mg of the compound per kilogram of body weight per day, or alternatively about 0.5 mg to about 50 g per patient per day.

Mastocytosis/mast cell leukemia, gastrointestinal stromal tumors (GIST), small cell lung carcinoma (SCLC), colon cancer, sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma may be effectively treated by the administration of from about 0.01 to 500 mg of the compound per kilogram of body weight per day, or alternatively about 0.5 mg to about 50 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention, or pharmaceutically acceptable salts or N-oxides thereof, can also be effectively administered in conjunction with other cancer therapeutic compounds. For example, cytotoxic agents and angiogenesis inhibiting agents can be advantageous co-agents with the compounds of the present invention. Accordingly, the present invention includes compositions comprising the compounds represented by Formula I, or a pharmaceutically acceptable salt or N-oxide thereof, and a cytotoxic agent or an angiogenesis-inhibiting agent. The amounts of each can be therapeutically effective alone—in which case the additive effects can overcome cancers resistant to treatment by monotherapy. The amounts of any can also be subtherapeutic—to minimize adverse effects, particularly in sensitive patients.

It is understood that the treatment of cancer depends on the type of cancer. For example, lung cancer is treated differently as a first line therapy than are colon cancer or breast cancer treated. Even within lung cancer, for example, first line therapy is different from second line therapy, which in turn is different from third line therapy. Newly diagnosed patients might be treated with cisplatinum containing regimens. Were that to fail, they move onto a second line therapy such as a taxane. Finally, if that failed, they might get a tyrosine kinase EGFR inhibitor as a third line therapy. Further, The regulatory approval process differs from country to country. Accordingly, the accepted treatment regimens can differ from country to country. Nevertheless, the compounds of the present invention, or pharmaceutically acceptable salts or N-oxides thereof, can be beneficially co-administered in conjunction or combination with other such cancer therapeutic compounds. Such other compounds include, for example, a variety of cytotoxic agents (alkylators, DNA topoisomerase inhibitors, antimetabolites, tubulin binders); inhibitors of angiogenesis; and different other forms of therapies including kinase inhibitors such as Tarceva, monoclonal antibodies, and cancer vaccines. Other such compounds that can be beneficially co-administered with the compounds of the present invention include doxorubicin, vincristine, cisplatin, carboplatin, gemcitabine, and the taxanes. Thus, the compositions of the present invention include a compound according to Formula I, or a pharmaceutically acceptable salt or N-oxide thereof, and an anti-neoplastic, anti-tumor, anti-angiogenic, or chemotherapeutic agent.

The compounds of the present invention, or pharmaceutically acceptable salts or N-oxides thereof, can also be effectively administered in conjunction with other therapeutic compounds, aside from cancer therapy. For example, therapeutic agents effective to ameliorate adverse side-effects can be advantageous co-agents with the compounds of the present invention.

I. Assay for Inhibition of c-Kit in Intact Cells

The ability of compounds to inhibit the tyrosine kinase activity of c-Kit was determined in a cell-based ELISA assay using the H526 cell line (ATCC # CRL-5811), which was originally derived from a human small cell lung cancer. The assay determines the ability of compounds to block ligand-stimulated tyrosine phosphorylation of the wild-type c-Kit receptor protein that is endogenously expressed in H526 cells. Cells are pre-incubated with compounds at various concentrations prior to addition of stem cell factor (SCF), the ligand for the c-Kit receptor tyrosine kinase. Cell lysates are then prepared and the c-Kit protein is captured onto a c-Kit antibody-coated 96-well ELISA plate. The phosphotyrosine content of the receptor protein is then monitored by quantitation of the degree of binding of an antibody that recognizes only the phosphorylated tyrosine residues within the captured protein. The antibody used has a reporter enzyme (e.g. horseradish peroxidase, HRP) covalently attached, such that binding of antibody to phosphorylated c-Kit can be determined quantitatively by incubation with an appropriate HRP substrate.

The stock reagents used are as follows:

Cell Lysis Buffer:
  50 mM Tris-HCl, pH 7.4
  150 mM NaCl
  10% Glycerol
  1% Triton X-100
  0.5 mM EDTA
  1 µg/mL leupeptin
  1 µg/mL aprotinin
  1 mM Sodium orthovanadate Anti c-Kit Antibody:
  0.5 µg/mL anti c-Kit Ab-3 (Lab Vision, catalog #MS289P1) in 50 mM Sodium bicarbonate, pH 9.

ELISA Assay Plates:
  ELISA assay plates are prepared by addition of 100 µL of anti c-Kit antibody to each well of a 96-well Microlite-2 plate (Dynex, catalog # 7417), followed by incubation at 37° C. for 2 h. The wells are then washed twice with 300 µL wash buffer.

Plate Wash Buffer:
  PBS containing 0.5% Tween-20 (PBST)

Cell Assay Medium:
  RPMI with 0.1% BSA pY20-HRP:
  25 ng/mL pY20-HRP (Calbiochem, catalog # 525320) in PBS, containing 0.5% Tween-20, 5% BSA, 1 mM Sodium orthovanadate HRP Substrate:
  Chemoluminescent detection reagent (Pierce, catalog # 37075)

Assay Protocol:
  Cultures of H526 cells, growing in RPMI with 10% fetal calf serum, were collected by centrifugation, washed twice with PBS, and suspended in cell assay medium. Cells were then distributed into a V-bottom 96-well plate at $7.5 \times 10^4$ cells per well in 100 µL cell assay medium.

Compound dilutions were prepared from 10 mM DMSO stocks by dilution in cell assay medium, the final concentration of DMSO in the assay being 0.1%. To compound incubation wells, 50 µL of the test compound was added (compounds are assayed at concentrations between 0.1 nM and 100 µM); to positive and negative control wells, 50 µL cell assay medium containing 0.1% DMSO was added. The cells were then incubated with compound at 37° C. for 3 h. SCF (R&D Systems, catalog #255-SC-010) was then added in order to stimulate the Kit receptor and induce its tyrosine phosphorylation. Then, 10 µL of a 1.6 µg/mL solution of SCF in cell assay medium was added to all wells apart from the negative control wells, and the cells were incubated for an additional 15 min at 37° C. Following the addition of ice-cold PBS, the plate was centrifuged at 1000 rpm for 5 min, the medium removed by aspiration, and the cell pellet lysed by the addition of 120 µL ice-cold cell lysis buffer per well. The plate was kept on ice for 20 min and 100 µL of the cell lysates from each well were then transferred to the wells of an ELISA assay plate and incubated at 4° C. for 16 h.

Following incubation of the cell lysates in the ELISA plate, the wells were washed 4 times with 300 µL wash buffer, then 100 µL of the phosphotyrosine detection antibody pY20-HRP was added to each well and the plate incubated at rt for 2 h. The wells were then washed 4 times with 300 µL wash buffer. Then, 50 µL of the chemiluminescent HRP substrate was added to each well for luminometric quantitation of the amount of antiphosphotyrosine-HRP conjugate bound to the plate.

Comparison of the assay signals obtained in the presence of compound with those of the positive and negative controls (cells incubated in the presence or absence of SCF, with no compound added), allows the degree of inhibition of c-Kit receptor tyrosine phosphorylation to be determined over a range of compound concentrations. These inhibition values were fitted to a sigmoidal dose-response inhibition curve to determine the $IC_{50}$ values (i.e. the concentration of compound that inhibits SCF-induced tyrosine phosphorylation of the c-Kit protein by 50%).

The EXAMPLES of this invention reduced the level of SCF-induced tyrosine phosphorylation of Kit in intact H526 cells as determined in the above assay with $IC_{50}$ values between 15 µM and 0.1 nM.

EXPERIMENTAL

The EXAMPLES of the present invention were prepared according to the following procedures by the methods illustrated in the following schemes. Appropriate solvents, temperatures, pressures and other reaction conditions may be readily selected by one of ordinary skill in the art. Similarly, suitable starting materials may be commercially obtained or readily prepared by one skilled in the art.

Scheme 1

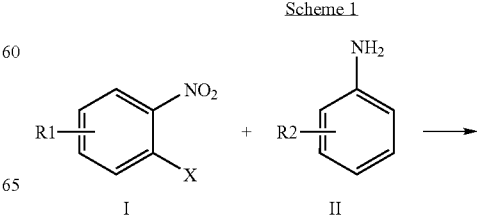

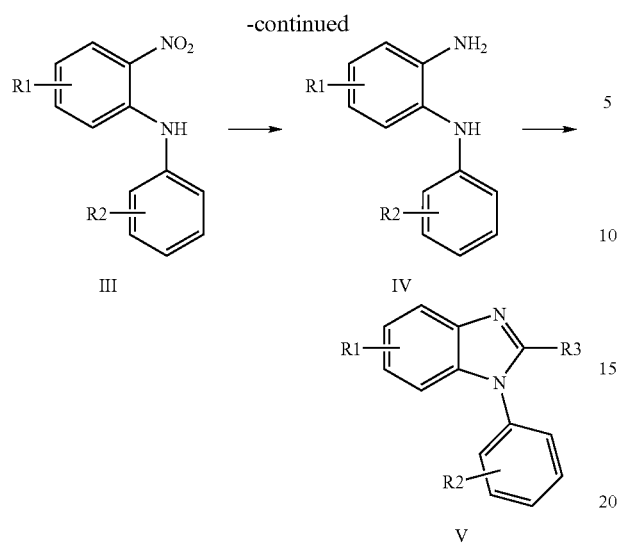

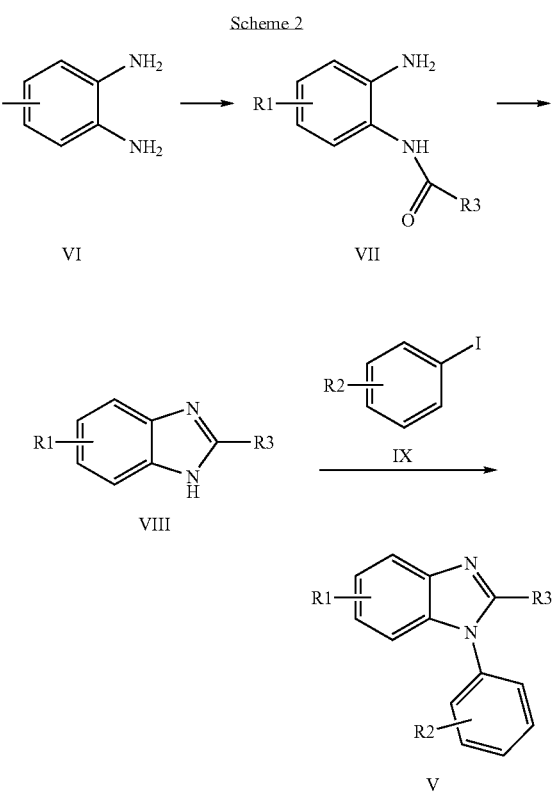

In Scheme 1, diarylamines (III) may be produced from the condensation of nitrobenzenes (I, X=F, OMS, OTs) with substituted anilines (II). Coupling of the anilines (II) may also be achieved where X=I, Br, Cl, OTf by utilisation of Pd(0) mediated Buchwald-Hartwig-type conditions (such as those described in *J. Organic Chem.*, (1996), 61(21), 7240) or with Cu(I) catalysts and base (e.g. $K_2CO_3$). Reduction of III to give the phenylenediamines (IV) may be achieved using for example, hydrogen in the presence of a suitable transition metal catalyst (palladium, platinum, ruthenium, nickel), iron, zinc or tin under acidic conditions, with sodium hydrosulphite or with tin(II)chloride dihydrate. Cyclisation of IV to the benzimidazoles (V) may be achieved by reaction with a corresponding carboxylic acid, acid halide, acid anhydride or an orthoformate (e.g. $(MeO)_3CH$) and an acid such as formic or p-toluenesulphonic acid. Under certain conditions used to reduce III e.g. iron powder in formic acid, conversion to the benzimidazoles V may be achieved in one pot. Also, by inclusion of trimethyl orthoformate into a hydrogenation mixture with III, allows the direct conversion to V.

Scheme 2 below shows that formation of N-arylbenzimidazoles (V) may also be accomplished via the process outlined, whereby $N^1H$ benzimidazoles (VIII) may be arylated under Pd(0) mediated conditions as disclosed in *J. Amer. Chem. Soc.*, (2000), 122, 7600. Separation of the resulting regioisomers may be achieved by a number of means known to those skilled in the art including, but not limited to, chromatographic means or through crystallisation from a suitable solvent. Benzimidazoles (VIII) may be produced from the cyclisation of the anilides (VII) with acids such as, but not limited to, acetic, p-toluenesulphonic, hydrochloric, sulphuric or phosphoric acid. In turn the anilides (VII) can be prepared by reaction of o-phenylenediamines with acid halides or anhydrides or with carboxylic acids in the presence of appropriate coupling reagents known to those skilled in the art such as, but not limited to, EDC, DCC, HOAt, HOBt, HATU, TBTU, or CDI including solid supported versions of these solution phase reagents. Where R3=H, compounds such as VII may be prepared by formylation of VI with alkyl formates (e.g. methyl formate). In the processes described, conversion of VI into VII may also lead to the partial or complete conversion to VIII.

Functionalities R1 and R2, may be included into the target molecules through appropriate choice of starting materials, e.g. of type I, II, VI and IX. Where the final functionality is not available directly through this process, or where such functionality may be compromised during the subsequent chemistry to build the final molecule, alternative functionalities may be used and subsequently transformed into the final desired functionality by methods, and at points in the sequence, readily determined by one skilled in the art.

For example, a non-exhaustive list of such transformations includes the conversions: OMe→OH ($BBr_3$), $NH_2$→Cl ($NaNO_2$, CuCl), Br→CN ($Pd_2(dba)_3$, $Zn(CN)_2$, DPPF), Me→$CO_2H$ ($KMnO_4$), $CO_2H$→$CO_2Me$ (MeOH, $H_2SO_4$), OH→OAlkyl (Alkyl halide, base), $CO_2H$→CONR'R" (EDC, HOAt, DIPEA, HNR'R"), Br→$CO_2Me$ ($Pd_2(dba)_3$, DPPF, CO(g), MeOH), Br→$CO_2H$ ($^tBuLi$, $CO_2$), Ar—H→Ar—Br (NBS), CN→$CO_2H$ (conc. $H_2SO_4$), Br→NR'R" ($Pd_2(dba)_3$, DPPF, HNR'R").

Representative examples of the incorporation of such functionality into target molecules are shown below in Schemes 3-5.

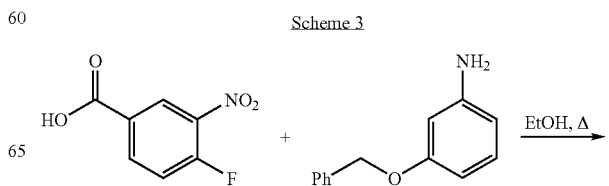

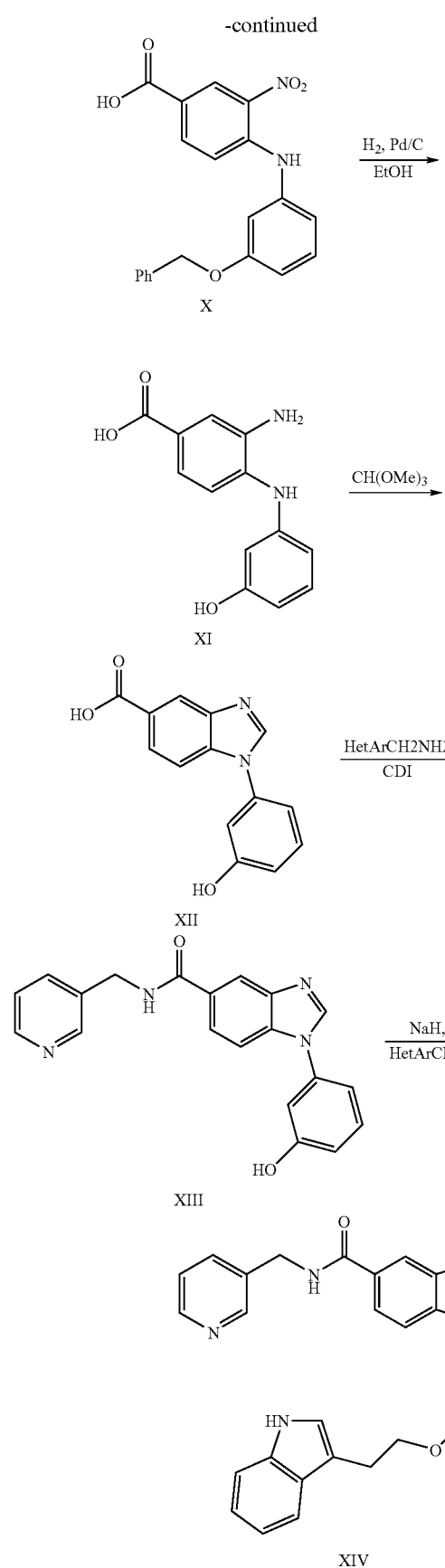

Condensation of 3-benzyloxyaniline with 4-fluoro-3-nitrobenzoic acid occurs through heating in ethanol to give X which may be reduced via catalytic hydrogenation over 10% Pd/C in ethanol to give the phenylenediamine (XI). Cyclisation of XI to the benzimidazole (XII) is achieved by heating with an excess of trimethylorthoformate. 1,1'-Carbonyldiimidazole mediated coupling with 3-pyridylmethylamine gives amide XIII which may be alkylated with 3-(2-chloroethyl)indole in the presence of sodium hydride.

Scheme 4

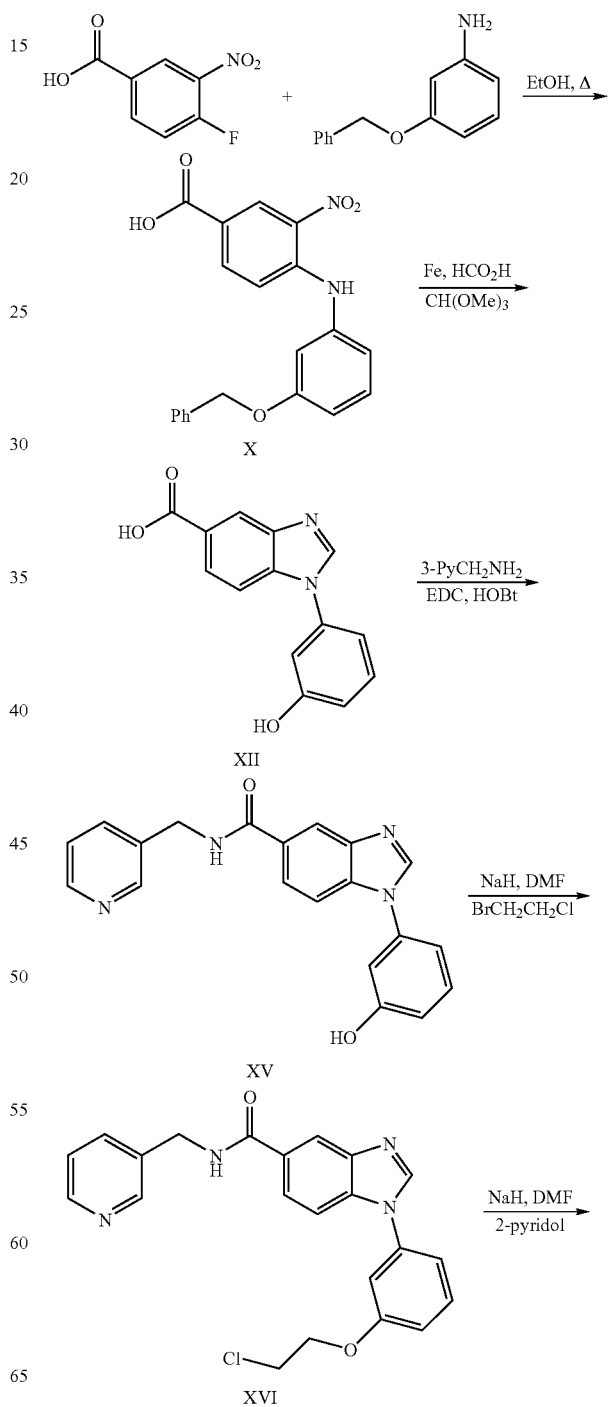

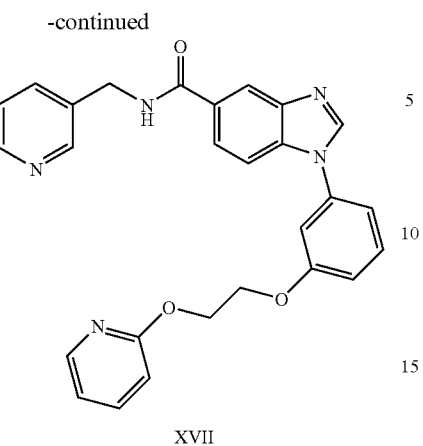

XVII

In Scheme 4 the aniline X is reduced and cyclised in one-pot using trimethylorthoformate in the presence of the iron and formic acid reducing mixture. The acid XII in this instance is coupled with 3-aminomethylpyridine utilising EDC and HOBt to give amide XV which is alkylated with 1-bromo-2-chloroethane and sodium hydride. The resulting haloalkyl derivative XVI is used to alkylate 2-pyridol, again using sodium hydride as base, to give the target molecule XVII.

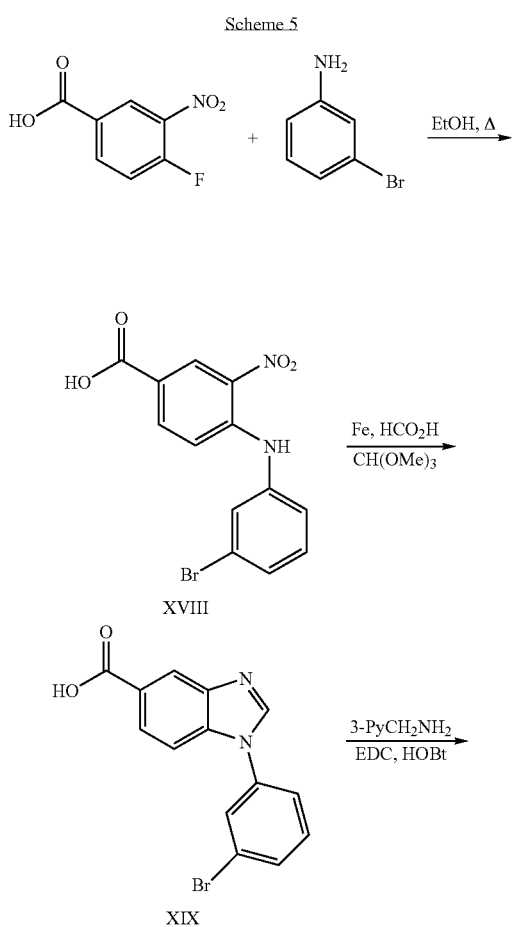

Scheme 5

XVIII

XIX

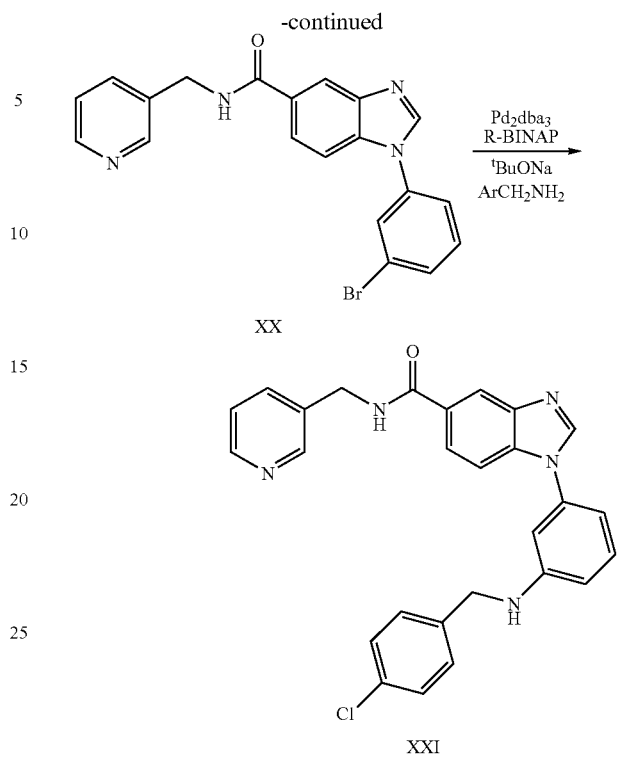

XX

XXI

Amino derivatives of the type XXI may be prepared as in Scheme 5 whereby the appropriate bromobenzimidazole (XX) is formed under the conditions employed for Scheme 4 and is subjected to Pd(0) mediated amination conditions to introduce, in this case, a substituted benzylamino group.

Definitions: EDC=ethyl dimethylaminopropylcarbodiimide hydrochloride, HOAt=1-hydroxyazabenzotriazole, HOBt=1-hydroxybenzotriazole, CDI=1,1'-carbonyldiimidazole, TBTU=O-benzotriazole-N,N,N',N'-tetramethyluronium tetrafluoroborate, HATU=azabenzotriazolyl-N,N,N',N', -tetramethyluronium hexafluorophosphate, DIPEA=diisopropylethylamine, TEA=triethylamine, DMF=N,N-dimethylformamide, NMP=N-methylpyrrolidinone, DCM=dichloromethane, DMAP=4-dimethylaminopyridine, TFA=trifluoroacetic acid, Boc=$^t$butoxycarbonyl, Fmoc=fluorenylmethyloxycarbonyl, DMSO=dimethylsulphoxide, OMs=OSO$_2$Me, OTs=OSO$_2$-(4-Me)Ph, OTf=OSO$_2$CF$_3$, DPPF=, Pd$_2$(dba)$_3$, NBS=N-bromosuccinimide, HCl (aq)=aqueous hydrochloric acid, DMA=N,N-dimethylacetamide, MeOH=methanol, EtOH=ethanol, EtOAc=ethyl acetate, DCM=dichloromethane, THF=tetrahydrofuran, HOAc=acetic acid, DMF=N,N-dimethylformamide, HPLC=high performance liquid chromatography, General Procedures for the Preparation of N-Substituted Benzimidazoles:

a) 3-Fluoro-2-nitrobenzoic acid (21.6 mmol) and an aniline (43.2 mmol) in 15 mL of ethanol were stirred at reflux under argon for 5 h resulting in the formation of an orange precipitate. After 12 h the heterogeneous reaction mixture was poured into 50 mL of 1N HCl(aq) and diluted with 100 mL of water. The solution was stirred for 20 min then the precipitate filtered to yield the 4-anilino-3-nitrobenzoic Acid: e.g. 4-{[3-(benzyloxy)phenyl]amino}-3-nitrobenzoic acid.

A solution of the 4-anilino-3-nitrobenzoic acid (20.1 mmol) in THF (100 mL) was charged with 10% Pd/C (500 mg) and the reaction flask evacuated and subsequently charged with $H_2$ (g) three times. The mixture was stirred vigorously for 12 h after which time it was filtered through diatomaceous earth and the filtrate concentrated in vacuo to give the desired 3-amino-4-anilinobenzoic acid: e.g. 3-amino-4-[(3-hydroxyphenyl)amino]benzoic acid.

c) A solution of 3-amino-4-anilinobenzoic acid (20.1 mmol) in formic acid (40 mL) was charged with trimethylorthoformate (2.4 mL, 22.0 mmol) and heated at reflux for 3 h after which time the mixture was allowed to cool to rt and stirred for 12 h. The reaction mixture was then poured into 150 mL of $H_2O$ and stirred for 20 min yielding a precipitate which was isolated by filtration to give the 1-aryl-1H-benzimidazole-5-carboxylic acid: e.g. 1-(3-hydroxyphenyl)-1H-benzimidazole-5-carboxylic acid.

d) A solution of the 1-aryl-1H-benzimidazole-5-carboxylic acid (0.39 mmol) in DMF (5 mL) was treated with CDI (95 mg, 0.58 mmol) and stirred for 15 min resulting in the formation of a white precipitate. A primary or secondary amine (0.78 mmol) was then added and the mixture was stirred overnight prior to being poured into 75 mL $H_2O$ and any solid subsequently formed, isolated by filtration to give the 1-aryl-N-(substituted)-1H-benzimidazole-5-carboxamide. Where the desired product did not precipitate from the reaction solution or during the work up, it was isolated by addition of water, extraction into organic solvent (typically EtOAc), drying and concentration of the extracts, and the residue then purified by preparative HPLC or by normal phase chromatography over silica gel.

e) Alternatively:

A solution of 1-aryl-1H-benzimidazole-5-carboxylic acid (0.78 mmol) in DMF (4 mL) was treated with EDC (227 mg, 1.18 mmol) and DMAP (9 mg, 0.07 mmol) and the mixture stirred for 10 min prior to the addition of a primary or secondary amine (1.68 mmol). The mixture was stirred overnight after which time product was isolated by filtration and the cake washed with methanol (3×5 mL) to give the desired 1-aryl-N-(substituted)-1H-benzimidazole-5-carboxamide.

Again, where the desired product did not precipitate from the reaction solution or during the work up, it was isolated by addition of water, extraction into organic solvent (typically EtOAc), drying and concentration of the extracts, and the residue then purified by preparative HPLC or by normal phase chromatography over silica gel.

[1] General Procedure for the Alkylation of N-(Hydroxyphenyl) Benzimidazole Derivatives:

f) A mixture of 1-(3-hydroxyphenyl)-N-pyridin-3-ylmethyl-1H-benzimidazole-5-carboxamide (prepared as described above, 75 mg, 0.22 mmol) and potassium carbonate (33 mg, 0.24 mmol) in acetonitrile (4 mL), DMF (1 mL), and distilled water (0.5 mL), was treated with an alkyl bromide (0.22 mmol) and the reaction mixture heated at 60° C. under $N_2$ for 16 h. The reaction mixture was then concentrated in vacuo and the residue subjected to reverse-phase preparative HPLC purification to give the 1-(3-alkyloxyphenyl)-N-pyridin-3-ylmethyl-1H-benzimidazole-5-carboxamide.

The following compounds were prepared according to the procedures described above utilizing an appropriately substituted phenol and alkylating agent in place of 1-(3-hydroxyphenyl)-N-pyridin-3-ylmethyl-1H-benzimidazole-5-carboxamide and the 'alkyl' bromide, respectively.

EXAMPLE 1

1-{3-[2-(Phenylthio)ethoxy]phenyl}-N-pyridin-3-ylmethyl-1H-benzimidazole-5-carboxamide; (DMSO-d6, 400 MHz): d 3.41 (t, 2H, J=6.4 Hz), 4.29 (t, 2H, J=6.4 Hz), 4.54 (d, 2H, J=6.0 Hz), 7.06 (dd, 1H, J=8.2, 2.4 Hz), 7.18-7.34 (m, 5H), 7.37 (dd, 2H, J=8.0, 4.8 Hz), 7.42 (d, 1H, J=8.0 Hz), 7.53 (dd, 1H, J=8.0, 8.0 Hz), 7.67 (d, 1H, J=8.4 Hz), 7.76 (d, 1H, J=7.6 Hz), 7.91 (dd, 1H, J=8.8, 1.6 Hz), 8.36 (s, 1H), 8.46 (d, 1H, J=3.6 Hz), 8.58 (s, 1H), 8.66 (s, 1H), 9.15 (t, 1H, J=6.0); MS (ES+): m/z 481 [MH$^+$]

EXAMPLE 2

1-[3-(3-phenylpropoxy)phenyl]-N-pyridin-3-ylmethyl-1H-benzimidazole-5-carboxamide. MS (ES+): m/z 463 [MH$^+$]

EXAMPLE 3

1-[3-(3-phenoxypropoxy)phenyl]-N-pyridin-3-ylmethyl-1H-benzimidazole-5-carboxamide. MS (ES+): m/z 479 [MH$^+$]

EXAMPLE 4

1-{3-[(4-Cyanobenzyl)oxy]phenyl}-N-pyridin-3-ylmethyl-1H-benzimidazole-5-carboxamide. MS (ES+): m/z 460 [MH$^+$]

EXAMPLE 5

Ethyl 5-[(3-{5-[(pyridin-3-ylmethylamino)carbonyl]-1H-benzimidazol-1-yl}phenoxy)methyl]-2-furoate. MS (ES+): m/z 497 [MH$^+$]

EXAMPLE 6

N-Pyridin-3-ylmethyl-1-(3-{[4-(trifluoromethoxy)benzyl]oxy}phenyl)-1H-benzimidazole-5-carboxamide. MS (ES+): m/z 519 [MH$^+$]

EXAMPLE 7

3-(3-{5-[(Pyridin-3-ylmethylamino)carbonyl]-1H-benzimidazol-1-yl}phenoxy)pentyl acetate. MS (ES+): m/z 473 [MH$^+$]

EXAMPLE 8

1-[3-(2-Naphthylmethoxy)phenyl]-N-pyridin-3-ylmethyl-1H-benzimidazole-5-carboxamide. MS (ES+): m/z 485 [MH$^+$]

EXAMPLE 9

N-Pyridin-3-ylmethyl-1-(3-{[4-(trifluoromethyl)benzyl]oxy}phenyl)-1H-benzimidazole-5-carboxamide. MS (ES+): m/z 503 [MH$^+$]

EXAMPLE 10

Ethyl 4-{3-[5-(pyridin-3-ylmethylaminocarbonyl)-1H-benzimidazol-1-yl]phenoxy}hexanoate. MS (ES+): m/z 487 [MH$^+$]

EXAMPLE 11

1-[3-(2-Morpholin-4-ylethoxy)phenyl]-N-pyridin-3-ylmethyl-1H-benzimidazole-5-carboxamide. MS (ES+): m/z 458 [MH$^+$]

EXAMPLE 12

1-{4-[(4-Fluorobenzyl)oxy]phenyl}-N-pyridin-3-ylmethyl-1H-benzimidazole-5-carboxamide. MS (ES+): m/z 452 [MH$^+$]

EXAMPLE 13

1-{4-[2-(Phenylthio)ethoxy]phenyl}-N-pyridin-3-ylmethyl-1H-benzimidazole-5-carboxamide. MS (ES+): m/z 481 [MH$^+$]

EXAMPLE 14

Methyl 4-[(4-{5-[(pyridin-3-ylmethylamino)carbonyl]-1H-benzimidazol-1-yl}phenoxy)methyl]benzoate. MS (ES+): m/z 493 [MH$^+$]

EXAMPLE 15

Ethyl 5-[(4-{5-[(pyridin-3-ylmethylamino)carbonyl]-1H-benzimidazol-1-yl}phenoxy)methyl]-2-furoate. MS (ES+): m/z 497 [MH$^+$]

EXAMPLE 16

1-{3-[(4-Methylbenzyl)oxy]phenyl}-N-pyridin-3-ylmethyl-1H-benzimidazole-5-carboxamide. MS (ES+): m/z 449 [MH$^+$]

EXAMPLE 17

1-{3-[(4-Nitrobenzyl)oxy]phenyl}-N-pyridin-3-ylmethyl-1H-benzimidazole-5-carboxamide. MS (ES+): m/z 480 [MH$^+$]

EXAMPLE 18

1-{4-[(4-Methylbenzyl)oxy]phenyl}-N-pyridin-3-ylmethyl-1H-benzimidazole-5-carboxamide. MS (ES+): m/z 449 [MH$^+$]

EXAMPLE 19

1-[3-(3-phenoxypropoxy)phenyl]-N-pyridin-3-ylmethyl-1H-benzimidazole-5-carboxamide. MS (ES+): m/z 479 [MH$^+$]

EXAMPLE 20

1-(4-{5-[(pyridin-3-ylmethylamino)carbonyl]-1H-benzimidazol-1-yl}phenoxy)pentyl acetate. MS (ES+): m/z 473 [MH$^+$]

EXAMPLE 21

Methyl 4-[(3-{5-[(pyridin-3-ylmethylamino)carbonyl]-1H-benzimidazol-1-yl}phenoxy)methyl]benzoate. MS (ES+): m/z 493 [MH$^+$]

EXAMPLE 22

1-[4-(2-Phenylethoxy)phenyl]-N-pyridin-3-ylmethyl-1H-benzimidazole-5-carboxamide. MS (ES+): m/z 449 [MH$^+$]

EXAMPLE 23

Ethyl 4-{4-[5-(pyridin-3-ylmethylaminocarbonyl)-1H-benzimidazol-1-yl]phenoxy}hexanoate. MS (ES+): m/z 487 [MH$^+$]

EXAMPLE 24

1-{4-[(4-Trifluoromethylbenzyl)oxy]phenyl}-N-pyridin-3-ylmethyl-1H-benzimidazole-5-carboxamide. MS (ES+): m/z 503 [MH$^+$]

EXAMPLE 25

1-[4-(2-naphthylmethoxy)phenyl]-N-pyridin-3-ylmethyl-1H-benzimidazole-5-carboxamide. MS (ES+): m/z 485 [MH$^+$]

EXAMPLE 26

1-[4-(1,1'-biphenyl-2-ylmethoxy)phenyl]-N-pyridin-3-ylmethyl-1H-benzimidazole-5-carboxamide. MS (ES+): m/z 511 [MH$^+$]

EXAMPLE 27

1-{4-[(4-Nitrobenzyl)oxy]phenyl}-N-pyridin-3-ylmethyl-1H-benzimidazole-5-carboxamide. MS (ES+): m/z 480 [MH$^+$]

EXAMPLE 28

1-[4-(Cyclohexylmethyloxy)phenyl]-N-pyridin-3-ylmethyl-1H-benzimidazole-5-carboxamide. MS (ES+): m/z 441 [MH$^+$]

EXAMPLE 29

1-[4-(1-Phenethylethoxy)phenyl]-N-pyridin-3-ylmethyl-1H-benzimidazole-5-carboxamide. MS (ES+): m/z 449 [MH$^+$]

EXAMPLE 30

1-[3-(1-Phenethylethoxy)phenyl]-N-pyridin-3-ylmethyl-1H-benzimidazole-5-carboxamide. MS (ES+): m/z 449 [MH$^+$]

EXAMPLE 31

1-[3-(2-Phenylethoxy)phenyl]-N-pyridin-3-ylmethyl-1H-benzimidazole-5-carboxamide. MS (ES+): m/z 449 [MH$^+$]

EXAMPLE 32

1-[4-(1,1'-Biphenyl-4-ylmethoxy)phenyl]-N-pyridin-3-ylmethyl-1H-benzimidazole-5-carboxamide. MS (ES+): m/z 511 [MH$^+$]

EXAMPLE 33

1-[4-(1H-Indol-3-ylmethoxy)phenyl]-N-pyridin-3-ylmethyl-1H-benzimidazole-5-carboxamide. MS (ES+): m/z 488 [MH$^+$]

EXAMPLE 34

1-[4-(2-Morpholin-4-ylethoxy)phenyl]-N-pyridin-3-ylmethyl-1H-benzimidazole-5-carboxamide. MS (ES+): m/z 458 [MH$^+$]

EXAMPLE 35

N-Pyridin-3-ylmethyl-1-(4-{[4-(trifluoromethoxy)benzyl]oxy}phenyl)-1H-benzimidazole-5-carboxamide. MS (ES+): m/z 519 [MH$^+$]

EXAMPLE 36

1-[4-(2-Phenoxyethoxy)phenyl]-N-pyridin-3-ylmethyl-1H-benzimidazole-5-carboxamide. MS (ES+): m/z 465 [MH$^+$]

EXAMPLE 37

1-[3-(2-Phenoxyethoxy)phenyl]-N-pyridin-3-ylmethyl-1H-benzimidazole-5-carboxamide. MS (ES+): m/z 465 [MH$^+$]

EXAMPLE 38

1-[3-(1H-Indol-3-ylmethoxy)phenyl]-N-pyridin-3-ylmethyl-1H-benzimidazole-5-carboxamide. MS (ES+): m/z 488 [MH$^+$]

EXAMPLE 39

1-{4-[3-(4-Fluorophenoxy)propoxy]phenyl}-N-pyridin-3-ylmethyl-1H-benzimidazole-5-carboxamide. MS (ES+): m/z 497 [MH$^+$]

EXAMPLE 40

1-{3-[3-(4-Fluorophenoxy)propoxy]phenyl}-N-pyridin-3-ylmethyl-1H-benzimidazole-5-carboxamide. MS (ES+): m/z 497 [MH$^+$]

EXAMPLE 41

1-{4-[2-(4-Fluorophenoxy)ethoxy]phenyl}-N-pyridin-3-ylmethyl-1H-benzimidazole-5-carboxamide. MS (ES+): m/z 544 [MH$^+$]

EXAMPLE 42

1-[3-(2-Methoxyethoxy)phenyl]-N-pyridin-3-ylmethyl-1H-benzimidazole-5-carboxamide. MS (ES+): m/z 403 [MH$^+$]

EXAMPLE 43

1-{4-[2-(2-Methoxyethoxy)ethoxy]phenyl}-N-pyridin-3-ylmethyl-1H-benzimidazole-5-carboxamide. MS (ES+): m/z 447 [MH$^+$]

EXAMPLE 44

1-[4-(2-Methoxyethoxy)phenyl]-N-pyridin-3-ylmethyl-1H-benzimidazole-5-carboxamide. MS (ES+): m/z 403 [MH$^+$]

EXAMPLE 45

1-{3-[2-(2-Methoxyethoxy)ethoxy]phenyl}-N-pyridin-3-ylmethyl-1H-benzimidazole-5-carboxamide. MS (ES+): m/z 447 [MH$^+$]

EXAMPLE 46

1-[4-(2-Ethoxyethoxy)phenyl]-N-pyridin-3-ylmethyl-1H-benzimidazole-5-carboxamide. MS (ES+): m/z 417 [MH$^+$]

EXAMPLE 47

1-[3-(2-Ethoxyethoxy)phenyl]-N-pyridin-3-ylmethyl-1H-benzimidazole-5-carboxamide. MS (ES+): m/z 417 [MH$^+$]

EXAMPLE 48

1-{3-[2-(4-Bromophenoxy)ethoxy]phenyl}-N-pyridin-3-ylmethyl-1H-benzimidazole-5-carboxamide. MS (ES+): m/z 543 [Br$^{79}$ MH$^+$], 545 [Br$^{81}$MH+]

EXAMPLE 49

1-{4-[2-(4-Bromophenoxy)ethoxy]phenyl}-N-pyridin-3-ylmethyl-1H-benzimidazole-5-carboxamide. MS (ES+): m/z 543 [Br$^{79}$ MH$^+$], 545 [Br$^{81}$MH+]

EXAMPLE 50

1-{4-[2-Methylthiazol-4-ylmethyl)oxy]phenyl}-N-pyridin-3-ylmethyl-1H-benzimidazole-5-carboxamide. MS (ES+): m/z 456 [MH$^+$]

EXAMPLE 51

1-{3-[(2-Methylthiazol-4-ylmethyl)oxy]phenyl}-N-pyridin-3-ylmethyl-1H-benzimidazole-5-carboxamide. MS (ES+): m/z 456 [MH$^+$]

EXAMPLE 52

1-{3-[(Quinolin-2-ylmethyl)oxy]phenyl}-N-pyridin-3-ylmethyl-1H-benzimidazole-5-carboxamide. MS (ES+): m/z 486 [MH$^+$]

EXAMPLE 53

1-{4-[(Quinolin-2-ylmethyl)oxy]phenyl}-N-pyridin-3-ylmethyl-1H-benzimidazole-5-carboxamide. MS (ES+): m/z 486 [MH$^+$]

EXAMPLE 54

1-{3-[2-(4-Chlorophenoxy)ethoxy]phenyl}-N-pyridin-3-ylmethyl-1H-benzimidazole-5-carboxamide. MS (ES+): m/z 499 [MH$^+$]

EXAMPLE 55

N-Pyridin-3-ylmethyl-1-(4-{3-[3-(trifluoromethoxy)phenoxy]propoxy}phenyl)-1H-benzimidazole-5-carboxamide.
1-[4-(2-Chloropropoxy)phenyl]-N-pyridin-3-ylmethyl-1H-benzimidazole-5-carboxamide (prepared as described above using 1-(4-hydroxyphenyl)-N-pyridin-3-ylmethyl-1H-benzimidazole-5-carboxamide as phenol and 1-bromo-3- chloropropane as alkylating agent) (100 mg, 0.24 mmol), 3-trifluoromethoxyphenol (42 mg, 31 μL 0.24 mmol) and potassium carbonate (36 mg, 0.26 mmol) were suspended in acetonitrile (2 mL), DMF (1 mL), and water (0.5 mL) and the mixture stirred at 60° C. for 18 h. The reaction mixture was then concentrated in vacuo and purified by reverse-phase preparative HPLC to give N-pyridin-3-ylmethyl-1-(4-{3-[3-(trifluoromethoxy) phenoxy]propoxy}phenyl)-1H-benzimidazole-5-carboxamide. $^1$H NMR (CDCl$_3$, 400 MHz): δ 8.66 (d, J=2.0 Hz, 1H), 8.56 (dd, J=4.8, 1.2 Hz, 1H), 8.34 (d, J=1.6 Hz, 1H), 8.05 (s, 1H), 7.90 (dd, J=8.4, 1.6 Hz, 1H), 7.78 (ddd, J=8.0, 2.0, 2.0 Hz, 1H), 7.48 (d, J=8.0 Hz, 1H), 7.43-7.37 (m, 2H), 7.34-7.28 (m, 2H), 7.20-7.08 (m, 3H), 6.90-6.78 (m, 3H), 4.75 (d, J=5.6 Hz, 2H), 4.27 (t, J=6.0 Hz, 2H), 4.22 (t, J=6.0 Hz, 2H), 2.35 (quin, J=6.0 Hz, 2H); MS (ES+): m/z 563 [MH$^+$]

The following compounds were prepared according to procedures analogous to those described above.

EXAMPLE 56

1-{4-[3-(3-Methoxyphenoxy}propoxy]phenyl}-N-pyridin-3-ylmethyl-1H-benzimidazole-5-carboxamide. MS (ES+): m/z 509 [MH$^+$]

EXAMPLE 57

1-{4-[3-(3-Chlorophenoxy)propoxy]phenyl}-N-pyridin-3-ylmethyl-1H-benzimidazole-5-carboxamide. MS (ES+): m/z 513 [MH$^+$], 515 [MH$^+$]

EXAMPLE 58

1-{4-[3-(4-Cyanophenoxy)propoxy]phenyl}-N-pyridin-3-ylmethyl-1H-benzimidazole-5-carboxamide. MS (ES+): m/z 504 [MH$^+$]

EXAMPLE 59

1-{4-[3-(4-Methoxyphenoxy)propoxy]phenyl}-N-pyridin-3-ylmethyl-1H-benzimidazole-5-carboxamide. MS (ES+): m/z 509 [MH$^+$]

EXAMPLE 60

1-{4-[3-(3-Methylphenoxy)propoxy]phenyl}-N-pyridin-3-ylmethyl-1H-benzimidazole-5-carboxamide. MS (ES+): m/z 493 [MH$^+$]

EXAMPLE 61

1-{4-[3-(3-Ethynylphenoxy)propoxy]phenyl}-N-pyridin-3-ylmethyl-1H-benzimidazole-5-carboxamide. MS (ES+): m/z 503 [MH$^+$]

EXAMPLE 62

1-{3-[3-(4-Methylphenoxy)propoxy]phenyl}-N-pyridin-3-ylmethyl-1H-benzimidazole-5-carboxamide. MS (ES+): m/z 493 [MH$^+$]

EXAMPLE 63

1-{3-[3-(4-Cyanophenoxy)propoxy]phenyl}-N-pyridin-3-ylmethyl-1H-benzimidazole-5-carboxamide. MS (ES+): m/z 504 [MH$^+$]

EXAMPLE 64

1-(3-{3-[3-(Trifluoromethoxy)phenoxy]propoxy}phenyl)-N-pyridin-3-ylmethyl-1H-benzimidazole-5-carboxamide. MS (ES+): m/z 563 [MH$^+$]

EXAMPLE 65

1-{3-[3-(3-Chlorophenoxy)propoxy]phenyl}-N-pyridin-3-ylmethyl-1H-benzimidazole-5-carboxamide. MS (ES+): m/z 513 [MH$^+$]

EXAMPLE 66

1-{3-[3-(4-Chlorophenoxy)propoxy]phenyl}-N-pyridin-3-ylmethyl-1H-benzimidazole-5-carboxamide. MS (ES+): m/z 513 [MH$^+$], 515 [MH$^+$]

EXAMPLE 67

1-{3-[3-(4-Bromophenoxy)propoxy]phenyl}-N-pyridin-3-ylmethyl-1H-benzimidazole-5-carboxamide. MS (ES+): m/z 557 [MH$^+$], 559 [MH$^+$]

EXAMPLE 68

1-(3-{3-[4-(Trifluoromethoxy)phenoxy]propoxy}phenyl)-N-pyridin-3-ylmethyl-1H-benzimidazole-5-carboxamide. MS (ES+): m/z 563 [MH$^+$]

EXAMPLE 69

1-{3-[3-(3,4-Dichlorophenoxy)propoxy]phenyl}-N-pyridin-3-ylmethyl-1H-benzimidazole-5-carboxamide. MS (ES+): m/z 547 [MH$^+$], 548 [MH$^+$]

EXAMPLE 70

1-{3-[3-(4-Imidazol-1-ylphenoxy)propoxy]phenyl}-N-pyridin-3-ylmethyl-1H-benzimidazole-5-carboxamide. MS (ES+): m/z 545 [MH$^+$]

EXAMPLE 71

1-(3-{3-[4-(4H-1,2,4-Triazol-4-yl)phenoxy]propoxy}phenyl)-N-pyridin-3-ylmethyl-1H-benzimidazole-5-carboxamide. MS (ES+): m/z 546 [MH$^+$]

EXAMPLE 72

1-(3-{3-[4-(Trifluoromethyl)phenoxy]propoxy}phenyl)-N-pyridin-3-ylmethyl-1H-benzimidazole-5-carboxamide. MS (ES+): m/z 550 [MH$^+$]

EXAMPLE 73

Methyl 4-(3-{3-[5-(N-pyridin-3-ylmethyl)aminocarbonyl]-1H-benzimidazol-1-ylphenoxy}propoxy)benzoate. MS (ES+): m/z 537 [MH$^+$]

EXAMPLE 74

1-{4-[3-(4-Bromophenoxy)propoxy]phenyl}-N-pyridin-3-ylmethyl-1H-benzimidazole-5-carboxamide. MS (ES+): m/z 557 [Br$^{79}$ MH$^+$], 559 [Br$^{81}$MH$^+$]

EXAMPLE 75

1-{3-[2-(4-Methylphenoxy)ethoxy]phenyl}-N-pyridin-3-ylmethyl-1H-benzimidazole-5-carboxamide.

1-(3-Hydroxyphenyl)-N-pyridin-3-ylmethyl-1H-benzimidazole-5-carboxamide (5.0 g, 14.5 mmol), tetrabutylammonium iodide (536 mg, 1.5 mmol) and sodium hydroxide (9.8 g, 41.7 mmol) were dissolved in anhydrous ethanol and heated to reflux for 15 min. 2-Chloroethyl tosylate (581 mg, 41.67 mmol, 7.6 mL) was then added and the mixture allowed to stir at 80° C. for 18 h. After this time, the reaction mixture was concentrated in vacuo and the crude product purified by chromatography over silica gel eluting with 50% ethyl acetate/hexanes to 10% methanol in ethyl acetate to give 1-[3-(2-chloroethoxy)phenyl]-N-pyridin-3-ylmethyl-1H-benzimidazole-5-carboxamide.

This material was reacted with 4-methylphenol using the previously described procedures to give the title compound. $^1$H NMR (CDCl$_3$, 400 MHz): δ 2.29 (s, 3H), 4.35 (dd, 2H, J=5.6, 2.8 Hz), 4.39 (dd, 2H, J=5.2, 3.2 Hz), 4.74 (d, 2H, J=5.6 Hz), 6.64 (dd, 1H, J=7.2, 7.2 Hz), 6.85 (ddd, 2H, J=9.6, 3.2, 3.2 Hz), 7.07-7.13 (m, 4H), 7.30 (dd, 1H, J=7.6, 4.8 Hz), 7.51 (dd, 1H, J=7.6, 7.6 Hz), 7.61 (d, 1H, J=8.8 Hz), 7.77 (dd, 1H, J=6.4, 1.6 Hz), 7.88 (dd, 1H, J=8.8, 2.0 Hz), 8.17 (s, 1H), 8.27 (s, 1H), 8.56 (dd, 1H, J=4.8, 1.6 Hz), 8.66 (d, 1H, J=2.0 Hz); MS (ES+): m/z 479 [MH$^+$]

The following compounds were prepared according to the previously described procedures, substituting the 1-(3-hydroxyphenyl)-N-pyridin-3-ylmethyl-1H-benzimidazole-5-carboxamide for 1-(4-hydroxyphenyl)-N-pyridin-3-ylmethyl-1H-benzimidazole-5-carboxamide where applicable, and 4-methylphenol for the appropriately substituted phenol.

EXAMPLE 76

1-{4-[2-(3-Chlorophenoxy)ethoxy]phenyl}-N-pyridin-3-ylmethyl-1H-benzimidazole-5-carboxamide. MS (ES+): m/z 499 [MH$^+$], 501 [MH$^+$]

EXAMPLE 77

1-{4-[2-(3-Ethynylphenoxy)ethoxy]phenyl}-N-pyridin-3-ylmethyl-1H-benzimidazole-5-carboxamide. MS (ES+): m/z 499 [MH$^+$]

EXAMPLE 78

1-{4-[2-(3-Bromophenoxy)ethoxy]phenyl}-N-pyridin-3-ylmethyl-1H-benzimidazole-5-carboxamide. MS (ES+): m/z 543 [Br$^{79}$ MH$^+$], 545 [Br$^{81}$ MH+]

EXAMPLE 79

1-{4-[2-(4-Cyanophenoxy)ethoxy]phenyl}-N-pyridin-3-ylmethyl-1H-benzimidazole-5-carboxamide. MS (ES+): m/z 490 [MH$^+$]

EXAMPLE 80

1-{4-[2-(4-Chlorophenoxy)ethoxy]phenyl}-N-pyridin-3-ylmethyl-1H-benzimidazole-5-carboxamide. MS (ES+): m/z 499 [Cl$^{35}$MH$^+$], 501 [Cl$^{37}$MH$^+$]

EXAMPLE 81

1-{4-[2-(4-Methoxyphenoxy)ethoxy]phenyl}-N-pyridin-3-ylmethyl-1H-benzimidazole-5-carboxamide. MS (ES+): m/z 495 [MH$^+$]

EXAMPLE 82

1-{4-[2-(3-Methylphenoxy)ethoxy]phenyl}-N-pyridin-3-ylmethyl-1H-benzimidazole-5-carboxamide. MS (ES+): m/z 479 [MH$^+$]

EXAMPLE 83

N-Pyridin-3-ylmethyl-1-(4-{2-[(3-trifluoromethoxy)phenoxy]ethoxy}phenyl)-1H-benzimidazole-5-carboxamide. MS (ES+): m/z 549 [MH$^+$]

EXAMPLE 84

1-{4-[2-(4-Methylphenoxy)ethoxy]phenyl}-N-pyridin-3-ylmethyl-1H-benzimidazole-5-carboxamide. MS (ES+): m/z 479 [MH$^+$]

EXAMPLE 85

1-{4-[2-(3-Methoxyphenoxy)ethoxy]phenyl}-N-pyridin-3-ylmethyl-1H-benzimidazole-5-carboxamide. MS (ES+): m/z 495 [MH$^+$]

EXAMPLE 86

1-{3-[2-(3-Chlorophenoxy)ethoxy]phenyl}-N-pyridin-3-ylmethyl-1H-benzimidazole-5-carboxamide. MS (ES+); m/z 499 [Cl$^{35}$MH$^+$], 501 [Cl$^{37}$MH$^+$]

EXAMPLE F1

1-[4-(Pyridin-3-ylmethoxy)phenyl]-N-pyridin-3-ylmethyl-1H-benzimidazole-5-carboxamide.

A mixture of 1-(4-hydroxyphenyl)-N-pyridin-3-ylmethyl-1H-benzimidazole-5-carboxamide (75 mg, 0.22 mmol), PS-triphenylphosphine resin (327 mg, 0.33 mmol), and 3-pyridinecarbinol (35 mg, 32 μL, 0.33 mmol) in anhydrous DMF (or THF) (2 mL) under N$_2$, was treated dropwise with DIAD (Diisopropyl azodicarboxylate) (66 mg, 0.33 mmol, 64 μL). The mixture was heated at 40° C. and stirred vigorously for 18 h under nitrogen, after which time it was concentrated in vacuo and the residue purified by reverse-phase preparative HPLC to give the title compound as an opaque glassy solid. $^1$H NMR (CDCl$_3$, 400 MHz): δ 8.74 (dd, J=2.4, 0.4 Hz, 1H), 8.67-8.62 (m, 2H), 8.53 (dd, J=4.8, 1.6 Hz, 1H), 8.37 (d, J=1.2 Hz, 1H), 8.03 (s, 1H), 7.92 (dd, J=8.8, 1.6 Hz, 1H), 7.84 (ddd, J=8.0, 2.4, 1.6 Hz, 1H), 7.77 (ddd, J=8.4, 1.6, 1.6 Hz, 1H), 7.59 (dd, J=8.4, 0.4 Hz, 1H), 7.45-7.35 (m, 4H), 7.32-7.26 (m, 2H), 7.20-7.13 (m, 2H), 5.18 (s, 2H), 4.74 (d, J=6.0 Hz, 2H); MS (ES+): m/z 436 (100) [MH$^+$], 437 (30) [MH$^+$2].

The following compounds were prepared according to the previously described procedures, replacing the 1-(4-hydroxyphenyl)-N-pyridin-3-ylmethyl-1H-benzimidazole-5-carboxamide and 3-pyridinecarbinol, for the appropriately substituted phenol and primary alcohol respectively.

EXAMPLE F2

1-[3-(1,1'-biphenyl-2-ylmethoxy)phenyl]-N-pyridin-3-ylmethyl-1H-benzimidazole-5-carboxamide. MS (ES+): m/z 511 [MH$^+$]

EXAMPLE F3

1-{3-[(3,4-Dimethoxybenzyl)oxy]phenyl}-N-pyridin-3-ylmethyl-1H-benzimidazole-5-carboxamide. MS (ES+): m/z 495 [MH$^+$]

EXAMPLE F4

1-[3-(Cyclobutylmethoxy)phenyl]-N-pyridin-3-ylmethyl-1H-benzimidazole-5-carboxamide. MS (ES+): m/z 413 [MH$^+$]

EXAMPLE F5

1-{3-[(4-Methoxybenzyl)oxy]phenyl}-N-pyridin-3-ylmethyl-1H-benzimidazole-5-carboxamide. MS (ES+): m/z 465 [MH$^+$]

EXAMPLE F6

1-{3-[(2-Methoxybenzyl)oxy]phenyl}-N-pyridin-3-ylmethyl-1H-benzimidazole-5-carboxamide. MS (ES+): m/z 465 [MH$^+$]

EXAMPLE F7

1-{3-[(4-Benzyloxy-3-methoxybenzyl)oxy]phenyl}-N-pyridin-3-ylmethyl-1H-benzimidazole-5-carboxamide. MS (ES+): m/z 571 [MH$^+$]

EXAMPLE F8

1-{3-[(4-{t-Butyl}benzyl)oxy]phenyl}-N-pyridin-3-ylmethyl-1H-benzimidazole-5-carboxamide. MS (ES+): m/z 491 [MH$^+$]

EXAMPLE F9

1-{3-[(4-Phenylbutyl)oxy]phenyl}-N-pyridin-3-ylmethyl-1H-benzimidazole-5-carboxamide. MS (ES+): m/z 477 [MH$^+$]

EXAMPLE F10

1-[3-(Pyridin-4-ylmethoxy)phenyl]-N-pyridin-3-ylmethyl-1H-benzimidazole-5-carboxamide. MS (ES+): m/z 436 [MH$^+$]

EXAMPLE F11

1-[3-(3-Pyridin-4-ylpropoxy)phenyl]-N-pyridin-3-ylmethyl-1H-benzimidazole-5-carboxamide. MS (ES+): m/z 464 [MH$^+$]

EXAMPLE F12

1-[3-(Pyridin-3-ylmethoxy)phenyl]-N-pyridin-3-ylmethyl-1H-benzimidazole-5-carboxamide. MS (ES+): m/z 436 [MH$^+$]

EXAMPLE F13

1-[4-(Pyridin-4-ylmethoxy)phenyl]-N-pyridin-3-ylmethyl-1H-benzimidazole-5-carboxamide. MS (ES+): m/z 436 [MH$^+$]

EXAMPLE F14

1-[4-(3-Pyridin-4-ylpropoxy)phenyl]-N-pyridin-3-ylmethyl-1H-benzimidazole-5-carboxamide. MS (ES+): m/z 464 [MH$^+$]

EXAMPLE F15

1-{4-[2-(4-Methylthiazol-5-yl)ethoxy]phenyl}-N-pyridin-3-ylmethyl-1H-benzimidazole-5-carboxamide. MS (ES+): m/z 470 [MH$^+$]

EXAMPLE F16

1-[3-(Furan-3-ylmethyl)oxy)phenyl]-N-pyridin-3-ylmethyl-1H-benzimidazole-5-carboxamide. MS (ES+): m/z 425 [MH$^+$]

EXAMPLE F17

N-pyridin-3-ylmethyl-1-{4-[(2-Thiophen-2-ylethyl)oxy]phenyl}-1H-benzimidazole-5-carboxamide. MS (ES+): m/z 455 [MH$^+$]

EXAMPLE F18

N-pyridin-3-ylmethyl-1-{3-[(2-Thiophen-2-ylethyl)oxy]phenyl}-1H-benzimidazole-5-carboxamide. MS (ES+): m/z 455 [MH$^+$]

EXAMPLE F19

N-pyridin-3-ylmethyl-1-{4-[(2-Thiophen-3-ylethyl)oxy]phenyl}-1H-benzimidazole-5-carboxamide. MS (ES+): m/z 455 [MH$^+$]

EXAMPLE F20

1-(3-{[1-(4-Chlorophenyl)cyclopropyl]methoxy}phenyl)-N-pyridin-3-ylmethyl-1H-benzimidazole-5-carboxamide. MS (ES+): m/z 509 [Cl$^{35}$MH$^+$], 511 [Cl$^{37}$MH$^+$]

EXAMPLE F21

1-(4-{[1-(4-Chlorophenyl)cyclopropyl]methoxy}phenyl)-N-pyridin-3-ylmethyl-1H-benzimidazole-5-carboxamide. MS (ES+): m/z 509 [Cl$^{35}$MH$^+$], 511 [Cl$^{37}$MH$^+$]

EXAMPLE F22

N-pyridin-3-ylmethyl-1-{3-[(2-Thiophen-3-ylethyl)oxy]phenyl}-1H-benzimidazole-5-carboxamide. MS (ES+): m/z 455 [MH$^+$]

EXAMPLE G1

N-(2-morpholin-4-ylethyl)-1-(4-{[4-(trifluoromethoxy)benzyl]oxy}phenyl)-1H-benzimidazole-5-carboxamide. MS (ES+): m/z 541 [MH$^+$]

a) A 0.02M methanolic solution of 1-(4-hydroxyphenyl)-1H-benzimidazole-5-carboxylic acid, (4.5 g, 17.7 mmol) was treated with 12M HCl (15 mL, 177 mmol) and the resulting mixture allowed heated at reflux (90° C.) for 2d. Upon completion of reaction, the mixture was concentrated in vacuo to afford methyl 1-(4-hydroxyphenyl)-1H-benzimidazole-5-carboxylate which was used without further purification. $^1$H NMR (DMSO-d$_6$, 400 MHz) δ 3.89 (s, 3H), 7.01 (d, 2H, J=8.8 Hz), 7.47 (d, 2H, J=8.8 Hz), 7.59 (d, 1H, J=8.4 Hz), 7.94 (dd, 1H, J=8.4 Hz, 1.2 Hz), 8.34 (d, 1H, J=1.2 Hz), 8.34 (s, 1H), 10.02 (s, 1H); MS (ES+): m/z 269 (MH$^+$).

A 0.2M DMF solution of methyl 1-(4-hydroxyphenyl)-1H-benzimidazole-5-carboxylate (3.0 g, 9.8 mmol) with KO$^t$Bu (2.2 g, 19.6 mmol) was stirred at rt for 20 min. prior to treatment with NaI (9.8 mmol, 1.47 g) and p-(trifluoromethoxy) benzylbromide (1.88 mL, 11.2 mmol). The mixture was heated at 60° C. for 24 h. after which the mixture was concentrated in vacuo, and the residue purified by chromatography over silica gel eluting with 1:1 EtOAc:Hexane to afford methyl 1-(4-{[4-(trifluoromethoxy)benzyl]oxy}phenyl)-1H-benzimidazole-5-carboxylate. $^1$H NMR (DMSO-d$_6$, 400 MHz) δ 3.89 (s, 3H), 5.26 (s, 2H), 7.26-7.29 (m, 2H), 7.43 (d, 2H, J=7.6 Hz), 7.61-7.65 (m, 5H), 7.86 (dd, 1H, J=8.8 Hz, 1.6 Hz), 8.35 (d, 1H, J=1.2 Hz), 8.65 (s, 1H); MS (ES+): m/z 443 (MH$^+$).

c) A 0.5M THF solution of methyl 1-(4-{[4-(trifluoromethoxy)benzyl]oxy}phenyl)-1H-benzimidazole-5-carboxylate (3.7 g, 8.4 mmol) was treated with 10M NaOH (8.4 mL, 84 mmol) and enough methanol to make the mixture homogeneous. The reaction mixture was then heated at 70° C. for 24 h, after which it was concentrated in vacuo, taken up in water and acidified to pH 4 with 2M HCl(aq). The resulting precipitate was filtered and washed with water to afford 1-(4-{[4-(trifluoromethoxy) benzyl]oxy}phenyl)-1H-benzimidazole-5-carboxylic acid. $^1$H NMR (DMSO-d$_6$, 400 MHz) δ 5.26 (s, 2H), 7.26-7.29 (m, 2H), 7.43 (d, 2H, J=8.0 Hz), 7.58 (d, 1H, J=8.0 Hz), 7.63-7.66 (m, 4H), 7.94 (dd, 1H, J=8.8 Hz, 1.6 Hz), 8.33 (d, 1H, J=0.8 Hz), 8.62 (s, 1H); MS (ES+): m/z 429 (MH$^+$).

d) A 0.3 M THF solution of 1-(4-{[4-(trifluoromethoxy) benzyl]oxy}phenyl)-1H-benzimidazole-5-carboxylic acid (100 mg, 0.23 mmol) and CDI (76 mg, 0.46 mmol) was stirred at 60° C. for 4 h, after which the mixture was treated with a primary or secondary amine (0.35 mmol) and heating continued for a further 16 h. After this time, the mixture was concentrated in vacuo and the resulting residue purified by chromatography over silica gel. Recrystallization of the eluted product afforded The following compounds were prepared according to the procedures described above for EXAMPLE G1 utilizing the appropriate alkyl halides and amines.

EXAMPLE G2

N-(3-Dimethylaminopropyl)-1-(4-{[4-(trifluoromethoxy)benzyl]oxy}phenyl)-1H-benzimidazole-5-carboxamide. MS (ES+): m/z 513 [MH$^+$]

EXAMPLE G3

N-(2-Dimethylaminoethyl)-1-(4-{[4-(trifluoromethoxy)benzyl]oxy}phenyl)-1H-benzimidazole-5-carboxamide. MS (ES+): m/z 499 [MH$^+$]

EXAMPLE G4

N-(3-Methoxypropyl)-1-(4-{[4-(trifluoromethoxy)benzyl]oxy}phenyl)-1H-benzimidazole-5-carboxamide. MS (ES+): m/z 500 [MH$^+$]

EXAMPLE G5

N-(2-Methoxyethyl)-1-(4-{[4-(trifluoromethoxy)benzyl]oxy}phenyl)-1H-benzimidazole-5-carboxamide. MS (ES+): m/z 486 [MH$^+$]

EXAMPLE G6

N-(2-Piperidin-1-ylethyl)-1-(4-{[4-(trifluoromethoxy)benzyl]oxy}phenyl)-1H-benzimidazole-5-carboxamide. MS (ES+): m/z 539 [MH$^+$]

EXAMPLE G7

1-(4-{[1-(4-{[4-(trifluoromethoxy)benzyl]oxy}phenyl)-1H-benzimidazol-5-yl]carbonyl}piperazin-1-yl)ethanol. MS (ES+): m/z 541 [MH$^+$]

EXAMPLE G8

N-[3-(4-Methylpiperazin-1-yl)propyl]-1-(4-{[4-(trifluoromethoxy) benzyl]oxy}phenyl)-1H-benzimidazole-5-carboxamide. MS (ES+): m/z 568 [MH$^+$]

EXAMPLE G9

N-(3-Morpholin-4-ylpropyl)-1-(4-{[4-(trifluoromethoxy) benzyl]oxy}phenyl)-1H-benzimidazole-5-carboxamide. MS (ES+): m/z 555 [MH$^+$]

EXAMPLE G10

1-{4-[2-(4-Fluorophenoxy)ethoxy]phenyl}-N-[3-(4-methylpiperazin-1-yl)propyl]-1H-benzimidazole-5-carboxamide. MS (ES+): m/z 532 [MH$^+$]

EXAMPLE G11

1-{4-[2-(4-Fluorophenoxy)ethoxy]phenyl}-N-(2-morpholin-4-ylethyl)-1H-benzimidazole-5-carboxamide. MS (ES+): m/z 505 [MH$^+$]

EXAMPLE G12

1-{4-[2-(4-Fluorophenoxy)ethoxy]phenyl}-N-[2-(N,N-dimethylamino)ethyl]-1H-benzimidazole-5-carboxamide. MS (ES+): m/z 463 [MH$^+$]

EXAMPLE G13

1-{4-[2-(4-Fluorophenoxy)ethoxy]phenyl}-N-[3-(N,N-dimethylamino)propyl]-1H-benzimidazole-5-carboxamide. MS (ES+): m/z 477 [MH$^+$]

EXAMPLE G14

1-{4-[2-(4-Fluorophenoxy)ethoxy]phenyl}-N-(3-methoxypropyl)-1H-benzimidazole-5-carboxamide. MS (ES+): m/z 464 [MH$^+$]

EXAMPLE G15

1-{4-[2-(4-Fluorophenoxy)ethoxy]phenyl}-N-(2-methoxyethyl)-1H-benzimidazole-5-carboxamide. MS (ES+): m/z 450 [MH$^+$]

EXAMPLE G16

1-{1-[(1-{4-[2-(4-Fluorophenoxy)ethoxy]phenyl}-1H-benzimidazol-5-yl)carbonyl]piperidin-4-yl}ethanol. MS (ES+): m/z 504 [MH$^+$]

EXAMPLE G17

1-{4-[2-(4-Fluorophenoxy)ethoxy]phenyl}-N-(2-piperidin-1-ylethyl)-1H-benzimidazole-5-carboxamide. MS (ES+): m/z 503 [MH$^+$]

EXAMPLE G18

1-{4-[2-(4-Fluorophenoxy)ethoxy]phenyl}-N-(3-morpholin-4-ylpropyl)-1H-benzimidazole-5-carboxamide. MS (ES+): m/z 519 [MH$^+$]

EXAMPLE G19

1-{4-[2-(4-Fluorophenoxy)ethoxy]phenyl}-N-ethyl-1H-benzimidazole-5-carboxamide. MS (ES+): m/z 420 [MH$^+$]

EXAMPLE G20

2-{1-[(1-{4-[2-(4-Fluorophenoxy)ethoxy]phenyl}-1H-benzimidazol-5-yl)carbonyl]piperazin-4-yl}ethanol. MS (ES+): m/z 505 [MH$^+$]

EXAMPLE G21

N-[(1-oxidopyridin-3-yl)methyl]-1-(4-{[4-(trifluoromethoxy) benzyl]oxy}phenyl)-1H-benzimidazole-5-carboxamide.

N-Pyridin-3-ylmethyl-1-(4-{[4-(trifluoromethoxy)benzyl]oxy}phenyl)-1H-benzimidazole-5-carboxamide (EXAMPLE 35, 31 mg, 0.060 mmol) was dissolved in DCM (3 mL) and treated with m-chloroperoxybenzoic acid (18 mg, 0.72 mmol) and the mixture stirred at rt for 4 h. After this time the mixture was concentrated in vacuo and the crude product purified by preparative HPLC to give the title compound. $^1$H NMR (CD$_3$OD, 400 MHz): δ 4.63 (s, 2H), 5.21 (s, 2H), 7.24 (d, 2H, J=9.2 Hz), 7.31 (d, 2H, J=8.4 Hz), 7.51-7.60 (m, 6H), 7.66 (d, 1H, J=8.0 Hz), 7.90 (dd, 1H, J=8.8, 1.6 Hz), 8.25 (d, 1H, J=6.0 Hz), 8.31 (s, 1H), 8.38 (s, 1H), 8.46 (s, 1H). MS (ES+); m/z 535 (100) [MH$^+$], 536 (25) [MH$^{+2}$].

EXAMPLE G22

N-(2-Pyrrolidin-1-ylethyl)-1-(4-{[4-(trifluoromethoxy) benzyl]oxy}phenyl)-1H-benzimidazole-5-carboxamide 1-(4-{[4-(Trifluoromethyl)benzyl]oxy}phenyl)-1H-benzimidazole-5-carboxylic acid (25 mg, 0.058 mmol), PS-TFP (37 mg, 0.053 mmol), and DMAP (4 mg, 0.032 mmol) were added to a 24 mL scintillation vial. CH$_2$Cl$_2$ (1 mL) and DMF (0.25 mL) were added and the vial was shaken for 5 min. DIC (33 mg, 0.263 mmol) was then added and the vial was shaken for 3 h. The resin was filtered and washed with DMF (3×1 mL), CH$_2$Cl$_2$ (3×1 mL), DMF (3×1 mL), and THF (3×1 mL). The resin was resuspended in DMF (1 mL) and then DIEA (10 μL, 0.058 mmol) and 2-pyrrolidin-1-ylethanamine (7 mg, 0.058 mmol) were added. After shaking for 48 h, the reaction was filtered and the resin washed with CH$_2$Cl$_2$. The filtrate was concentrated in vacuo. The resultant crude white solid was purified using the Waters mass-directed HPLC purification system to give N-(2-pyrrolidin-1-ylethyl)-1-(4-{[4-(trifluoromethoxy) benzyl]oxy}phenyl)-1H-benzimidazole-5-carboxamide as an off-white solid. MS (ES+): m/z 526 (100) [MH$^+$].

EXAMPLE G23

N-Isopropyl-1-(4-{[4-(difluoromethoxy)benzyl]oxy}phenyl)-1H-benzimidazole-5-carboxamide; MS (ES+): m/z 452 [MH$^+$].

EXAMPLE G24

N-(1-Tetrahydro-2H-pyran-4-ylmethyl)-1-(4-{[4-(difluoromethoxy) benzyl]oxy}phenyl)-1H-benzimidazole-5-carboxamide; MS (ES+): m/z 508 [MH$^+$].

EXAMPLE G25

N-Isopropyl-1-(4-{[4-(trifluoromethyl)benzyl]oxy}phenyl)-1H-benzimidazole-5-carboxamide; MS (ES+): m/z 454 [MH$^+$].

EXAMPLE G26

N-[3-(Dimethylamino)propyl]-1-{4-[2-(4-fluorophenoxy)ethoxy]phenyl}-1H-benzimidazole-5-carboxamide; MS (ES+): m/z 477 [MH$^+$].

EXAMPLE G27

(4-{[1-([2-(4-Fluorophenoxy)ethoxy]phenyl)-1H-benzimidazol-5-yl]carbonyl}piperazin-1-yl)ethanol; MS (ES+): m/z 505.1 [MH$^+$].

EXAMPLE G28

N-Ethyl-1-{4-[2-(4-fluorophenoxy)ethoxy]phenyl}-1H-benzimidazole-5-carboxamide; MS (ES+): m/z 420 [MH$^+$].

EXAMPLE G29

N-(2-Pyrrolidin-1-ylethyl)-1-(4-{[4-(trifluoromethyl) benzyl]oxy}phenyl)-1H-benzimidazole-5-carboxamide; MS (ES+): m/z 509 [MH$^+$].

EXAMPLE G30

N-(2-Hydroxyethyl)-1-(4-{[4-(trifluoromethyl)benzyl]oxy}phenyl)-1H-benzimidazole-5-carboxamide; MS (ES+): m/z 456 [MH$^+$].

EXAMPLE G31

N-[3-(Dimethylamino)propyl]-1-(4-{[4-(trifluoromethoxy)benzyl]oxy}phenyl)-1H-benzimidazole-5-carboxamide; MS (ES+): m/z 499 [MH$^+$].

EXAMPLE G32

1-{4-[3-(4-Fluorophenoxy)propoxy]phenyl}-N-(3-methoxypropyl)-1H-benzimidazole-5-carboxamide; MS (ES+): m/z 478 [MH$^+$].

EXAMPLE G33

1-{4-[3-(4-Fluorophenoxy)propoxy]phenyl}-N-(2-methoxyethyl)-1H-benzimidazole-5-carboxamide; MS (ES+): m/z 464 [MH$^+$].

EXAMPLE G34

1-{4-[3-(4-Fluorophenoxy)propoxy]phenyl}-N-(3-morpholin-4-ylpropyl)-1H-benzimidazole-5-carboxamide; MS (ES+): m/z 533 [MH$^+$].

EXAMPLE G35

1-{4-[3-(4-Fluorophenoxy)propoxy]phenyl}-N-(2-morpholin-4-ylethyl)-1H-benzimidazole-5-carboxamide; MS (ES+): m/z 519 [MH$^+$].

EXAMPLE G36

N-[2-(Dimethylamino)ethyl]-1-{4-[3-(4-fluorophenoxy)propoxy]phenyl}-1H-benzimidazole-5-carboxamide; MS (ES+): m/z 477 [MH$^+$].

EXAMPLE G37

N-(2-Methoxyethyl)-1-(3-{[4-(trifluoromethoxy)benzyl]oxy}phenyl)-1H-benzimidazole-5-carboxamide; MS (ES+): m/z 486 [MH$^+$].

EXAMPLE G38

N-[2-(Dimethylamino)ethyl]-1-(3-{[4-(trifluoromethoxy)benzyl]oxy}phenyl)-1H-benzimidazole-5-carboxamide; MS (ES+): m/z 499 [MH$^+$].

EXAMPLE G39

N-(2-Morpholin-4-ylethyl)-1-(3-{[4-(trifluoromethoxy)benzyl]oxy}phenyl)-1H-benzimidazole-5-carboxamide; MS (ES+): m/z 541 [MH$^+$].

EXAMPLE G40

N-[3-(4-Methylpiperazin-1-yl)propyl]-1-(3-{[4-(trifluoromethoxy) benzyl]oxy}phenyl)-1H-benzimidazole-5-carboxamide; MS (ES+): m/z 568 [MH$^+$].

EXAMPLE G41

N-Methyl-1-(3-{[4-(trifluoromethoxy)benzyl]oxy}phenyl)-1H-benzimidazole-5-carboxamide; MS (ES+) m/z 442 [MH$^+$]. $^1$H NMR (DMSO-d$_6$, 400 MHz): δ 2.82 (d, J=4.5 Hz, 3H), 5.28 (s, 2H), 7.17 (dd, J=8.4, 2.3 Hz, 1H), 7.29 (d, J=7.8 Hz, 1H), 7.37 (t, J=2.2 Hz, 1H), 7.43 (s, 1H), 7.45 (s, 1H), 7.60 (m, 4H), 7.85 (dd, J=8.6, 1.5 Hz, 1H), 8.29 (d, J=1.4 Hz, 1H), 8.51 (brs, 1H), 8.67 (s, 1H).

EXAMPLE G42

N-(1-Tetrahydro-2H-pyran-4-ylmethyl)-1-(4-{[4-(trifluoromethoxy) benzyl]oxy}phenyl)-1H-benzimidazole-5-carboxamide; MS (ES+): m/z 526 [MH$^+$].

EXAMPLE G43

N-[2-(1H-Imidazol-2-yl)ethyl]-1-(4-{[4-(trifluoromethoxy)benzyl]oxy}phenyl)-1H-benzimidazole-5-carboxamide; MS (ES+): m/z 522 [MH$^+$].

EXAMPLE G44

N-(2-Hydroxyethyl)-1-(4-{[4-(trifluoromethoxy)benzyl]oxy}phenyl)-1H-benzimidazole-5-carboxamide; MS (ES+): m/z 472 [MH$^+$].

EXAMPLE G45

N-(3-Hydroxypropyl)-1-(4-{[4-(trifluoromethoxy)benzyl]oxy}phenyl)-1H-benzimidazole-5-carboxamide; MS (ES+): m/z 486 [MH$^+$].

EXAMPLE G46

1-{4-[3-(4-Fluorophenoxy)propoxy]phenyl}-N-(2-hydroxyethyl)-1H-benzimidazole-5-carboxamide; MS (ES+): m/z 450 [MH$^+$].

EXAMPLE G47

1-{4-[3-(4-Fluorophenoxy)propoxy]phenyl}-N-(2-piperidin-1-ylethyl)-1H-benzimidazole-5-carboxamide; MS (ES+): m/z 517 [MH$^+$].

EXAMPLE G48

N-(3-Morpholin-4-ylpropyl)-1-(3-{[4-(trifluoromethoxy)benzyl]oxy}phenyl)-1H-benzimidazole-5-carboxamide; MS (ES+): m/z 555 [MH$^+$].

EXAMPLE G49

N-[3-(Dimethylamino)propyl]-1-(3-{[4-(trifluoromethoxy)benzyl]oxy}phenyl)-1H-benzimidazole-5-carboxamide; MS (ES+): m/z 513 [MH$^+$].

EXAMPLE G50

N-(3-Methoxypropyl)-1-(3-{[4-(trifluoromethoxy)benzyl]oxy}phenyl)-1H-benzimidazole-5-carboxamide; MS (ES+): m/z 500 [MH$^+$].

EXAMPLE G51

5-(Morpholin-4-ylcarbonyl)-1-(3-{[4-(trifluoromethoxy)benzyl]oxy}phenyl)-1H-benzimidazole; MS (ES+): m/z 498 [MH$^+$].

EXAMPLE G52

(4-{[1-(3-{[4-(Trifluoromethoxy)benzyl]oxy}phenyl)-1H-benzimidazol-5-yl]carbonyl}piperazin-1-yl)ethanol; MS (ES+): m/z 541 [MH$^+$].

EXAMPLE G53

(1-{[1-(3-{[4-(Trifluoromethoxy)benzyl]oxy}phenyl)-1H-benzimidazol-5-yl]carbonyl}piperidin-4-yl)ethanol; MS (ES+): m/z 540 [MH$^+$].

EXAMPLE G54

N-(2-Piperidin-1-ylethyl)-1-(3-{[4-(trifluoromethoxy)benzyl]oxy}phenyl)-1H-benzimidazole-5-carboxamide; MS (ES+): m/z 539 [MH$^+$].

EXAMPLE G55

5-[4-(2-Methoxyethyl)piperazin-1-ylcarbonyl]-1-[3-(4-trifluoromethoxy-benzyloxy)-phenyl]-1H-benzimidazole; MS (ES+): m/z 555 [MH$^+$].

EXAMPLE G56

N-Ethyl-1-(3-{[4-(trifluoromethoxy)benzyl]oxy}phenyl)-1H-benzimidazole-5-carboxamide; MS (ES+): m/z 456 [MH$^+$].

EXAMPLE G57

1-{3-[3-(4-Fluorophenoxy)propoxy]phenyl}-N-[3-(4-methylpiperazin-1-yl)propyl]-1H-benzimidazole-5-carboxamide; MS (ES+): m/z 532 [MH$^+$].

EXAMPLE G58

1-{3-[3-(4-Fluorophenoxy)propoxy]phenyl}-N-(3-morpholin-4ylpropyl)-1H-benzimidazole-5-carboxamide; MS (ES+): m/z 519 [MH$^+$].

EXAMPLE G59

N-[2-(Dimethylamino)ethyl]-1-{3-[2-(4-fluorophenoxy)ethoxy]phenyl}-1H-benzimidazole-5-carboxamide; MS (ES+): m/z 463 [MH$^+$].

EXAMPLE G60

N-[3-(Dimethylamino)propyl]-1-{3-[2-(4-fluorophenoxy)ethoxy]phenyl}-1H-benzimidazole-5-carboxamide; MS (ES+): m/z 477 [MH$^+$].

EXAMPLE G61

1-{3-[2-(4-Fluorophenoxy)ethoxy]phenyl}-N-(2-methoxyethyl)-1H-benzimidazole-5-carboxamide; MS (ES+): m/z 450 [MH$^+$].

EXAMPLE G62

1-{3-[2-(4-Fluorophenoxy)ethoxy]phenyl}-N-tetrahydro-2H-pyran-4-yl-1H-benzimidazole-5-carboxamide; MS (ES+): m/z 476 [MH$^+$].

EXAMPLE G63

1-{3-[2-(4-Fluorophenoxy)ethoxy]phenyl}-N-(1-tetrahydro-2H-pyran-4-ylmethyl)-1H-benzimidazole-5-carboxamide; MS (ES+): m/z 490 [MH$^+$].

EXAMPLE G64

N-Tetrahydro-2H-pyran-4-yl-1-(4-{[4-(trifluoromethoxy)benzyl]oxy}phenyl)-1H-benzimidazole-5-carboxamide; MS (ES+): m/z 513 [MH$^+$].

EXAMPLE G65

N-Cyclobutyl-1-(4-{[4-(trifluoromethoxy)benzyl]oxy}phenyl)-1H-benzimidazole-5-carboxamide; MS (ES+): m/z 482 [MH$^+$].

EXAMPLE G66

N-Isopropyl-1-[4-({4-[(trifluoromethyl)thio]benzyl}oxy)phenyl]-1H-benzimidazole-5-carboxamide; MS (ES+): m/z 486 (100) [MH$^+$].

EXAMPLE G67

N-(2-Morpholin-4ylethyl)-1-[4-({4-[(trifluoromethyl)thio]benzyl}oxy) phenyl]-1H-benzimidazole-5-carboxamide; MS (ES+): m/z 558 (100) [MH$^+$].

EXAMPLE G68

N-Methyl-1-[4-({4-[(trifluoromethyl)thio]benzyl}oxy)phenyl]-1H-benzimidazole-5-carboxamide; MS (ES+): m/z 458 (100) [MH$^+$].

EXAMPLE G69

N-(2-Pyrrolidin-1-ylethyl)-1-[4-({4-[(trifluoromethyl)thio]benzyl}oxy)phenyl]-1H-benzimidazole-5-carboxamide; MS (ES+): m/z 542 (100) [MH$^+$].

EXAMPLE G70

N-(2-Hydroxyethyl)-1-[4-({4-[(trifluoromethyl)thio]benzyl}oxy)phenyl]-1H-benzimidazole-5-carboxamide; MS (ES+): m/z 488 (100) [MH$^+$].

EXAMPLE G71

N-(1-Tetrahydro-2H-pyran-4-ylmethyl)-1-[4-({4-[(trifluoromethyl)thio]benzyl}oxy)phenyl]-1H-benzimidazole-5-carboxamide; MS (ES+): m/z 528 (100) [MH$^+$].

EXAMPLE G72

N-(2-Methoxyethyl)-1-(4-{[4-(trifluoromethyl)benzyl]oxy}phenyl)-1H-benzimidazole-5-carboxamide; MS (ES+): m/z 470 [MH$^+$].

EXAMPLE G73

1-(4-{[4-(Trifluoromethyl)benzyl]oxy}phenyl)-1H-benzimidazole-5-carboxamide; MS (ES+): m/z 412 [MH$^+$].

EXAMPLE G74

N-Methyl-1-(4-{[4-(trifluoromethyl)benzyl]oxy}phenyl)-1H-benzimidazole-5-carboxamide; MS (ES+): m/z 426[MH$^+$].

EXAMPLE G75

N-(2-Morpholin-4ylethyl)-1-(4-{[4-(trifluoromethyl)benzyl]oxy}phenyl)-1H-benzimidazole-5-carboxamide; MS (ES+): m/z 525 [MH$^+$].

EXAMPLE G76

N-(1-Tetrahydro-2H-pyran-4-ylmethyl)-1-(4-{[4-(trifluoromethyl) benzyl]oxy}phenyl)-1H-benzimidazole-5-carboxamide; MS (ES+): m/z 510 [MH$^+$].

EXAMPLE G77

N-Ethyl-1-[4-({4-[(trifluoromethyl)thio]benzyl}oxy)phenyl]-1H-benzimidazole-5-carboxamide; MS (ES+): m/z 559 (100) [MH$^+$].

EXAMPLE G78

1-[4-({4-[(Trifluoromethyl)thio]benzyl}oxy)phenyl]-1H-benzimidazole-5-carboxamide; MS (ES+): m/z 444 (100) [MH$^+$].

EXAMPLE G79

1-(4-{[4-(Difluoromethoxy)benzyl]oxy}phenyl)-1H-benzimidazole-5-carboxamide; MS (ES+): m/z 410 [MH$^+$].

EXAMPLE G80

N-Methyl-1-(4-{[4-(difluoromethoxy)benzyl]oxy}phenyl)-1H-benzimidazole-5-carboxamide; MS (ES+): m/z 424 [MH$^+$].

EXAMPLE G81

N-(2-Morpholin-4ylethyl)-1-(4-{[4-(difluoromethoxy)benzyl]oxy}phenyl)-1H-benzimidazole-5-carboxamide; MS (ES+): m/z 523 [MH$^+$].

EXAMPLE G82

N-(2-Pyrrolidin-1-ylethyl)-1-(4-{[4-(difluoromethoxy)benzyl]oxy}phenyl)-1H-benzimidazole-5-carboxamide; MS (ES+): m/z 507 [MH$^+$].

EXAMPLE G83

N-(2-Methoxyethyl)-1-(4-{[4-(difluoromethoxy)benzyl]oxy}phenyl)-1H-benzimidazole-5-carboxamide; MS (ES+): m/z 468 [MH$^+$].

EXAMPLEs H1 & H2

N-Pyridin-3-ylmethyl-1-{4-[3-(pyridin-2-yloxy)propoxy]phenyl}-1H-benzimidazole-5-carboxamide and 1-{4-[3-(2-oxopyridin-1 (2H)-yl)propoxy]phenyl}-N-pyridin-3-ylmethyl-1H-benzimidazole-5-carboxamide 1-[4-(3-Chloropropoxy)phenyl]-N-pyridin-3-ylmethyl-1H-benzimidazole-5-carboxamide (185 mg, 0.44 mmol), 2-pyridinol (42 mg, 0.44 mmol), cesium carbonate (156 mg, 0.48 mmol) and sodium iodide (72 mg, 0.48 mmol) were dissolved in DMF (4 mL) and the mixture heated at 80° C. under $N_2$ for 16 h. After this time the reaction mixture was concentrated in vacuo and subjected to reverse-phase preparative HPLC purification to afford isolation of N-pyridin-3-ylmethyl-1-{4-[3-(pyridin-2-yloxy)propoxy]phenyl}-1H-benzimidazole-5-carboxamide; MS (ES+): m/z 480 [MH$^+$] and 1-{4-[3-(2-Oxopyridin-1(2H)-yl)propoxy]phenyl}-N-pyridin-3-ylmethyl-1H-benzimidazole-5-carboxamide; MS (ES+): m/z 480 [MH$^+$]

The following examples were prepared according to the procedure described above for EXAMPLES H1 & H2 utilizing the appropriate alkyl halide and pyridinol in place of 1-[4-(3-Chloropropoxy)phenyl]-N-pyridin-3-ylmethyl-1H-benzimidazole-5-carboxamide and 2-pyridinol, respectively.

EXAMPLE H3

N-Pyridin-3-ylmethyl-1-{3-[3-(pyridin-2-yloxy)propoxy]phenyl}-1H-benzimidazole-5-carboxamide. MS (ES+): m/z 480 [MH$^+$]

EXAMPLEs H4 & H5

N-Pyridin-3-ylmethyl-1-{4-[2-(pyridin-2-yloxy)ethoxy]phenyl}-1H-benzimidazole-5-carboxamide. MS (ES+): m/z 466 [MH$^+$] and 1-{4-[2-(2-Oxopyridin-1 (2H)-yl)ethoxy]phenyl}-N-pyridin-3-ylmethyl-1H-benzimidazole-5-carboxamide. MS (ES+): m/z 466 [MH$^+$]

EXAMPLE H6

N-Pyridin-3-ylmethyl-1-{4-[2-(pyridin-3-yloxy)ethoxy]phenyl}-1H-benzimidazole-5-carboxamide. MS (ES+): m/z 466 [MH$^+$]

EXAMPLE H7

N-Pyridin-3-ylmethyl-1-{3-[3-(pyridin-3-yloxy)propoxy]phenyl}-1H-benzimidazole-5-carboxamide. MS (ES+): m/z 480 [MH$^+$]

EXAMPLE H8

1-{4-[2-(4-Oxopyridin-1 (4H)-yl)ethoxy]phenyl}-N-pyridin-3-ylmethyl-1H-benzimidazole-5-carboxamide. MS (ES+): m/z 466 [MH$^+$]

EXAMPLE H9

1-(4-{2-[2-Oxo-5-(trifluoromethyl)pyridin-1 (2H)-yl]ethoxy}phenyl)-N-pyridin-3-ylmethyl-1H-benzimidazole-5-carboxamide. MS (ES+): m/z 534 [MH$^+$]

EXAMPLEs H10 & H11

N-Pyridin-3-ylmethyl-1-{4-[2-(5-chloropyridin-2-yloxy)ethoxy]phenyl}-1H-benzimidazole-5-carboxamide; MS (ES+): m/z 500 [MH$^+$] and 1-{4-[2-(5-Chloro-2-oxopyridin-1 (2H)-yl)ethoxy]phenyl}-N-pyridin-3-ylmethyl-1H-benzimidazole-5-carboxamide. MS (ES+): m/z 500 [MH$^+$]

EXAMPLE H12

5-(2-{4-[5-(Pyridin-3-ylmethylaminocarbonyl)-1H-benzimidazol-1-yl]phenoxy}ethoxy)nicotinic acid An aqueous solution of sodium hydroxide (0.107 mmol, 43 µL, 100 mg/mL) was added to methyl 5-(2-{4-[5-(pyridin-3-ylmethylaminocarbonyl)-1H-benzimidazol-1-yl]phenoxy}ethoxy)nicotinate (prepared according to the procedure described above utilising methyl 5-hydroxynicotinate in place of 3-hydroxypyridine, 37 mg, 0.07 mmol) in methanol and the mixture heated at reflux for 18 h. The mixture was then concentrated in vacuo and purified by preparative HPLC to yield the title compound. $^1$H NMR (d$_6$-DMSO, 400 MHz): δ 9.15 (t, J=6.0 Hz, 1H), 8.64 (s, 1H), 8.60-8.50 (m, 2H), 8.40-8.39 (m, 2H), 8.38 (d, J=1.6 Hz, 1H), 8.35 (s, 1H), 7.87 (dd, J=8.4, 1.6 Hz, 1H), 7.78 (s, 1H), 7.73 (d, J=7.6 Hz, 1H), 7.59 (dd, J=12.4, 8.8 Hz, 3H), 7.35 (dd, J=7.6, 5.2 Hz, 1H), 7.23 (d, J=8.8 Hz, 2H), 4.51 (d, J=6.0 Hz, 2H), 4.50-4.4 (m, 4H); MS (ES+): m/z 510 [MH$^+$], 511 [MH$^{+2}$].

Compound H13

N-Pyridin-3-ylmethyl-1-{4-[2-(3-chloro-5-trifluoromethylpyridin-2-yloxy)ethoxy]phenyl}-1H-benzimidazole-5-carboxamide; MS (ES+): m/z 568 [MH$^+$], 570 [MH$^{+2}$]. This compound displayed results greater than 10 µM in the assay above.

EXAMPLE I1

1-{3-[(4-Chlorobenzyl)amino]phenyl}-N-pyridin-3-ylmethyl-1H-benzimidazole-5-carboxamide a) A mixture of 4-fluoro-3-nitrobenzoic acid (5) (10.2 g, 54.9 mmol), N-(3-aminophenyl)acetamide (9.21 g, 66.6 mmol) and Et$_3$N (1.4 mL, 10.1 mmol) in anhydrous EtOH (160 mL) was heated at reflux under $N_2$ overnight. The reaction mixture was then cooled and filtered, and the orange solid collected by filtration. It was then washed with 2 M HCl(aq), and dried in vacuo to give 4-{[3-(acetylamino)phenyl]amino}-3-nitrobenzoic acid. $^1$H NMR (400 MHz, DMSO-d$_6$): δ 2.03 (s, 3H), 7.02 (d, J=7.9 Hz, 1H), 7.13 (d, J=9.0 Hz, 1H), 7.37 (t, J=8.0 Hz, 1H), 7.42 (d, J=8.0 Hz, 1H), 7.68 (s, 1H), 7.93 (dd, J=9.0, 1.9 Hz, 1H), 8.62 (s, 1H), 9.76 (s, 1H), 10.08 (s, 1H), 13.02 (br, 1H); MS (ES+): m/z 316 [MH$^+$]

b) A suspension of 4-{[3-(acetylamino)phenyl]amino}-3-nitrobenzoic acid (1.27 g, 4.04 mmol), Fe (1.77 g, 31.6 mmol, powder) in HCO$_2$H (30 mL) and HC(OMe)$_3$ (20 mL) was stirred under $N_2$ at rt for 18 h. After this time, the reaction mixture was filtered through Celite, the cake washed with EtOH and the filtrate concentrated in vacuo. The resultant crude material was purified by column chromatography over silica gel eluting with 10% MeOH in DCM to afford 1-[3-(acetylamino)phenyl]-1H-benzimidazole-5-carboxylic acid. $^1$H NMR (400 MHz, DMSO-d$_6$): δ 2.07 (s, 3H), 7.36 (d, J=8.4 Hz, 1H), 7.56 (t, J=8.0 Hz, 1H), 7.63 (d, J=8.4 Hz, 1H), 7.69 (d, J=8.8 Hz, 1H), 7.96 (d, J=8.8 Hz, 1H), 8.02 (s, 1H), 8.34 (s, 1H), 8.71 (s, 1H), 10.3 (s, 1H); MS (ES+): m/z 296 [MH$^+$]

c) DIPEA (0.75 mL, 4.31 mmol) was added at rt to a mixture of 1-[3-(acetylamino)phenyl]-1H-benzimidazole-5-carboxylic acid (0.83 g, 2.8 mmol), EDC (0.81 g, 4.22 mmol), HOBt (0.57 g, 4.22 mmol) in anhydrous DMA (10 mL). The reaction mixture was stirred for 30 min prior to the dropwise addition of 3-aminomethylpyridine (0.57 mL, 5.62 mmol). After stirring for a further 25 h, the solvent was removed in vacuo and the crude material purified by column chromatography over silica gel eluting with 5-15% MeOH in DCM. The product was further purified by recrystallisation from acetone to afford 1-[3-(acetylamino)phenyl]-N-(pyridin-3-ylmethyl)-1H-benzimidazole-5-carboxamide. $^1$H NMR (400 MHz, DMSO-d$_6$): δ 2.09 (3H, s), 4.54 (d, J=6.0 Hz, 2H), 7.35-7.4 (m, 2H), 7.56 (t, J=8.0 Hz, 1H), 7.62 (d, J=7.6 Hz, 1H), 7.70 (d, J=8.4 Hz, 1H), 7.76 (d, J=8.4 Hz, 1H), 7.92 (dd, J=8.4 Hz, 1.2 Hz, 1H), 8.04 (t, J=2.0 Hz, 1H), 8.38 (d, J=1.2 Hz, 1H), 8.46 (dd, J=4.8 Hz, 1.6 Hz, 1H), 8.58 (1H, J=1.6 Hz, 1H), 8.68 (s, 1H), 9.21 (t, J=5.6 Hz, 1H), 10.33 (s, 1H); MS (ES+): m/z 386 [MH$^+$]

d) A solution of 1-[3-(acetylamino)phenyl]-N-(pyridin-3-ylmethyl)-1H-benzimidazole-5-carboxamide (0.47 g) in 2M HCl(aq) (5 mL) was heated at reflux until complete consumption of the starting material as judged by LC-MS (approximately 40 min). The crude reaction mixture was concentrated in vacuo and the residue dried in vacuo to afford 1-(3-aminophenyl)-N-(pyridin-3-ylmethyl)-1H-benzimidazole-5-carboxamide that was used without further purification. $^1$H-NMR (DMSO-d$_6$, 400 MHz): δ 3.5-5.5 (br), 4.72 (d, J=5.2 Hz, 2H), 7.24 (d, J=7.6 Hz, 1H), 7.39 (d, J=7.6 Hz, 1H), 7.44 (s, 1H), 7.56 (t, J=8.4 Hz, 1H), 7.82 (d, J=8.4 Hz, 1H), 8.10-8.50 (m, 2H), 8.47 (s, 1H), 8.59 (d, J=8.0 Hz, 1H), 8.85 (1H, J=5.6 Hz, 1H), 8.96 (s, 1H), 9.25 (s, 1H), 9.64 (t, J=5.6 Hz, 1H). MS (ES+): m/z 344 [MH$^+$]

e) A mixture of 1-(3-aminophenyl)-N-(pyridin-3-ylmethyl)-1H-benzimidazole-5-carboxamide (1.0 eq) and 4-chlorobenzaldehyde (1.0 eq) in MeOH:HOAc (10:1 v/v, 0.017M) was stirred for 15 min at rt prior to the addition of (polystyrylmethyl)trimethylammonium cyanoborohydride (3.5-5.0 mmol/g, 2.5 eq). The reaction mixture was shaken at rt overnight in a capped vial and then filtered through a plug of cotton wool. The resin was washed with MeOH and the combined filtrate and MeOH washings were concentrated under reduced pressure and purified by silica gel chromatography eluting with 5% MeOH in DCM to yield 1-{3-[(4-chlorobenzyl)amino]phenyl}-N-pyridin-3-ylmethyl-1H-benzimidazole-5-carboxamide. $^1$H-NMR (CD$_3$OD, 400 MHz): δ 4.38 (s, 2H), 4.89 (s, 2H), 6.68 (s, 1H), 6.76 (dd, J=2.0 Hz, 7.0 Hz, 2H), 7.20-7.45 (m, 7H), 7.81 (dd, J=8.4 Hz, 1.6 Hz, 1H), 7.89 (d, J=6.0 Hz, 1H), 8.26 (d, J=1.2 Hz, 1H), 8.42 (s, 1H), 8.45 (d, J=4 Hz, 1H), 8.60 (s, 1H). MS (ES+): m/z 469 [MH$^+$]

The following compounds were prepared according to the procedures described above for EXAMPLE I1, utilising the appropriate aldehydes in place of 4-chlorobenzaldehyde.

EXAMPLE I2

1-{3-[(4-Bromobenzyl)amino]phenyl}-N-pyridin-3-ylmethyl-1H-benzimidazole-5-carboxamide. MS (ES+): m/z 513 [MH$^+$]

EXAMPLE I3

1-{3-[(3-Methoxybenzyl)amino]phenyl}-N-pyridin-3-ylmethyl-1H-benzimidazole-5-carboxamide. MS (ES+): m/z 464 [MH$^+$]

EXAMPLE I4

1-{3-[(Pyridin-4-ylmethyl)amino]phenyl}-N-pyridin-3-ylmethyl-1H-benzimidazole-5-carboxamide. MS (ES+): m/z 435 [MH$^+$]

EXAMPLE I5

1-{3-[(Pyridin-3-ylmethyl)amino]phenyl}-N-pyridin-3-ylmethyl-1H-benzimidazole-5-carboxamide.

A solution of 1-(3-aminophenyl)-N-(pyridin-3-ylmethyl)-1H-benzimidazole-5-carboxamide (prepared in Steps (a)-(d) of the procedure used for the synthesis of EXAMPLE I1, 70.2 mg, 0.205 mmol) and nicotinaldehyde (20 μL, 0.21 mmol) in DCM (1 mL) under N$_2$ was treated with TFA (1 mL) and after 5 min was heated at reflux for 2 h. The cooled reaction mixture was then treated with Et$_3$SiH (70 μL, 0.44 mmol) and the mixture re-heated to reflux for 19 h. After this time the solvents and excess reagents were removed by concentration in vacuo and the crude residue purified by column chromatography over silica gel eluting with 0.7-15% MeOH/DCM to provide the title compound; MS (ES+): m/z 435 [MH$^+$]

EXAMPLE M1

1-{4-[2-(Pyrazin-2-yloxy)ethoxy]phenyl}-N-(pyridin-3-ylmethyl)-1H-benzimidazole-5-carboxamide

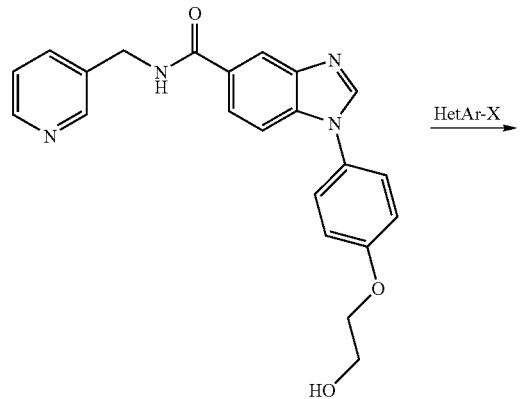

a) 1-(3-Hydroxyphenyl)-N-pyridin-3-ylmethyl-1H-benzimidazole-5-carboxamide (EXAMPLE B25, 2 g, 5.81 mmol), potassium carbonate (4.41 g, 31.94 mmol) and sodium iodide (1.92 g, 12.77 mmol) were dissolved in DMF (100 mL). 2-Bromoethanol (3.63 g, 17.42 mmol) was added drop-wise and the reaction was heated at 80° C. under N$_2$ atmosphere for 16 h. The reaction mixture was concentrated in vacuo and the crude reaction mixture was purified by silica gel chromatography (1:1 ethyl acetate/hexanes to 1:9 methanol/ethyl acetate) to obtain a mixture of 1-[4-(2-hydroxyethoxy)phenyl]-N-(pyridin-3-ylmethyl)-1H-benzimidazole-5-carboxamide and 1-{4-[2-(2-hydroxyethoxy)ethoxy]phenyl}-N-pyridin-3-ylmethyl-1H-benzimidazole-5-carboxamide dialkylated byproduct as a viscous brown solid. The mixture was carried onto the next step without further purification. MS(ES+): m/z 389.27 (100) [MH$^+$].

b) 1-[4-(2-Hydroxyethoxy)phenyl]-N-(pyridin-3-ylmethyl)-1H-benzimidazole-5-carboxamide (100 mg, 0.26 mmol) and sodium hydride (6 mg, 0.26 mmol) were dissolved in anhydrous DMF (2 mL) under N$_2$ atmosphere. The reaction mixture was heated to 60° C. until hydrogen gas evolution ceased. 2-Chloropyrazine (35 mg, 0.31 mmol, 28 μL) was then added drop-wise and the reaction was heated to 100° C. After 18 h, the reaction mixture was concentrated in vacuo and purified by mass-directed purification to provide 1-{4-[2-(Pyrazin-2-yloxy)ethoxy]phenyl}-N-(pyridin-3-ylmethyl)-1H-benzimidazole-5-carboxamide (OSIP484814AA) as a white powder. $^1$H NMR (d$_6$-DMSO, 400 MHz): δ 9.17 (brt, J=6.0 Hz, 1H), 8.60 (s, 1H), 8.58 (d, J=1.6 Hz, 1H), 8.47 (dd, J=5.2, 1.2 Hz, 1H), 8.40 (d, J=0.8 Hz, 1H), 8.37 (d, J=1.2 Hz, 1H), 8.26 (s, 2H), 7.90 (dd, J=8.6, 1.8 Hz, 1H), 7.76 (ddd, J=8.2, 1.8 Hz, 1H), 7.65-7.55 (m, 3H), 7.37 (ddd, J=8.0, 4.8, 0.8 Hz, 1H), 7.24 (ddd, J=9.2, 2.2, 2.2 Hz, 2H), 4.69 (m, 2H), 4.54 (d, J=4.4 Hz, 2H), 4.47 (m, 2H). MS(ES+): m/z 467 (100) [MH$^+$].

The following compound was prepared according to the procedure described above for EXAMPLE M1 utilizing 2-chloropyrimidine in place of 2-chloropyrazine.

EXAMPLE M2

1-{4-[2-(Pyrimidin-2-yloxy)ethoxy]phenyl}-N-(pyridin-3-ylmethyl)-1H-benzimidazole-5-carboxamide; MS(ES+): m/z 467 [MH$^+$].

EXAMPLE N1

N-Methyl-1-{4-[2-(pyridin-2-yloxy)ethoxy]phenyl}-1H-benzimidazole-5-carboxamide

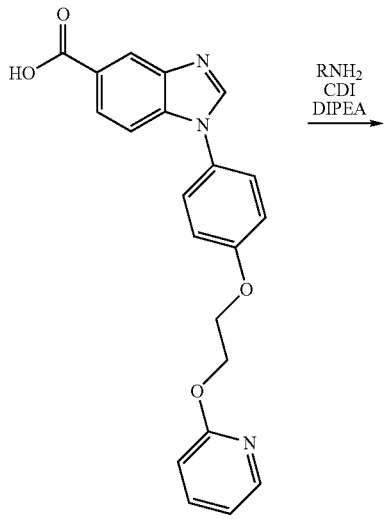

a) Ethylene glycol (30.1 g, 484 mmol), 2-chloropyridine (10.0 g, 88 mmol), powdered potassium hydroxide (9.9 g, 176.13 mmol), and 18-crown-6 ether (9.3 g, 35 mmol) were dissolved in anhydrous toluene (500 mL) under a N$_2$ atmosphere. The reaction mixture was stirred vigorously and heated to reflux. After 48 h, the reaction reached 50% conversion. The reaction mixture was concentrated in vacuo to approximately 100 mL volume then diluted with water (100 mL). After stirring for 0.5 h, the organic layer was separated and the aqueous layer was extracted with CH$_2$Cl$_2$. The organic extracts were combined, dried over anhydrous Na$_2$SO$_4$, and concentrated in vacuo. The crude product was purified by Jones column chromatography (100% hexanes to 50% ethyl acetate/hexanes) to give 2-(pyridin-2-yloxy)ethanol as a dark brown oil containing 15% w/w of 18-crown-6 ether. $^1$H NMR (d$_6$-DMSO, 400 MHz): δ 8.14 (ddd, J=5.0, 2.0, 1.2 Hz, 1H), 7.68 (ddd, J=9.4, 7.2, 2.4 Hz, 1H), 6.95 (ddd, J=8.0, 4.8, 1.2 Hz, 1H), 6.80 (ddd, J=8.4, 1.0, 1.0 Hz, 1H), 4.83 (t, J=5.6 Hz, 1H), 4.26 (t, J=5.2 Hz, 2H), 3.70 (dt, J=10.4, 5.2 Hz, 2H).

b) To a suspension of sodium hydride (21.6 mg, 0.90 mmol) in anhydrous DMF (0.5 mL), 2-(pyridin-2-yloxy)-ethanol (100 mg, 0.72 mmol) in DMF (1.5 mL) was added drop-wise under a N$_2$ atmosphere. Once hydrogen gas evolution ceased, 4-nitrofluorobenzene (102 mg, 0.72 mmol, 76 μL) was added drop-wise to the yellow suspension. The resultant red-orange solution was allowed to stir at rt for 18 h. Upon completion, distilled water (2 mL) was added and the bright yellow solid precipitate was filtered, washed with distilled water, and dried in vacuo to give 2-[2-(4-nitrophenoxy)ethoxy]pyridine as a pale yellow solid. $^1$H NMR (d$_6$-DMSO, 400 MHz): δ 8.21 (ddd, J=5.6, 3.6, 3.6 Hz, 2H), 7.72 (ddd, J=9.2, 7.2, 2.0 Hz, 1H), 7.21 (ddd, J=5.6, 3.6, 3.6 Hz, 1H), 7.01 (ddd, J=7.0, 4.8, 0.8 Hz, 1H), 6.86 (ddd, J=8.4, 0.8, 0.8 Hz, 1H), 4.62 (m, 2H), 4.49 (m, 2H). MS(ES+): m/z 261 [MH$^+$].

c) 2-[2-(4-Nitrophenoxy)ethoxy]pyridine (100 mg, 0.38 mmol) and tin (II) chloride dihydrate (433 mg, 1.92 mmol) were dissolved in ethanol (1.5 mL) and refluxed under nitrogen for 18 h. The reaction mixture was basified to pH 12 with 3M aqueous sodium hydroxide solution. The reaction mixture was stirred for 1 h and then filtered through Celite. The reaction mixture was concentrated in vacuo and the aqueous layer was separated and extracted with CH$_2$Cl$_2$ (5×). The combined organic extracts were concentrated in vacuo to give 4-[2-(pyridin-2-yloxy)ethoxy]aniline as a purple glassy solid. $^1$H NMR (d$_6$-DMSO, 400 MHz): δ 8.16 (ddd, J=5.2, 2.0, 0.8 Hz, 1H), 7.71 (ddd, J=9.2, 7.2, 2.0 Hz, 1H), 6.99 (ddd, J=7.2, 5.2, 1.0 Hz, 1H), 6.85 (ddd, J=8.4, 0.8, 0.8 Hz, 1H), 6.68 (ddd, J=5.6, 3.6, 3.6 Hz, 2H), 6.50 (ddd, J=5.6, 3.6, 3.6 Hz, 2H), 4.62 (brs, 2H), 4.50 (m, 2H), 4.15 (m, 2H).

d) 4-[2-(Pyridin-2-yloxy)ethoxy]aniline (4.50 g, 19.50 mmol) and 4-fluoro-3-nitrobenzoic acid (3.60 g, 19.50 mmol) were dissolved in ethanol (100 mL) and refluxed under nitrogen for 18 h. The reaction mixture was filtered and washed with cold ethanol (×2) to give 3-nitro-4-({4-[2-(pyridin-2-yloxy)ethoxy]phenyl}amino) benzoic acid as a reddish orange solid. $^1$H NMR (d$_6$-DMSO, 400 MHz): δ 9.77 (brs, 1H), 8.64 (d, J=2.4 Hz, 1H), 8.18 (ddd, J=5.2, 2.0, 0.8 Hz, 1H), 7.88 (dd, J=9.6, 2.0 Hz, 1H), 7.73 (ddd, J=8.8, 6.8, 2.0 Hz, 1H), 7.29 (ddd, J=6.4, 3.2, 3.2 Hz, 1H), 7.08 (ddd, J=5.6, 3.2, 3.2 Hz, 1H), 7.01 (ddd, J=7.4, 5.2, 1.2 Hz, 1H), 6.97 (d, J=9.2 Hz, 1H), 6.87 (ddd, J=8.4, 0.8, 0.8 Hz, 1H), 4.60 (m, 2H), 4.37 (m, 2H), 4.15 (m, 2H). MS(ES+): m/z 396.45 (100) [MH$^+$].

e) 3-Nitro-4-({4-[2-(pyridin-2-yloxy)ethoxy]phenyl}amino)benzoic acid (6.00 g, 15.20 mmol), iron powder (8.49 g, 152.00 mmol), and formic acid (68 mL) were dissolved in dry trimethyl orthoformate (175 mL). The reaction was allowed to stir at rt. After 18 h, the reaction mixture was diluted with CH$_2$Cl$_2$ and filtered through Celite to give a bright orange solid. The crude mixture was recrystallized from methanol to give 1-{4-[2-(pyridin-2-yloxy)ethoxy]phenyl}-1H-benzimidazole-5-carboxylic acid as a yellow-tan powder. $^1$H NMR (d$_6$-DMSO, 400 MHz): δ 8.61 (d, J=2.4 Hz, 1H), 8.32 (d, J=1.6 Hz, 1H), 8.19 (ddd, J=5.2, 1.6, 0.8 Hz, 1H), 7.93 (dd, J=8.8, 1.6 Hz, 1H), 7.73 (ddd, J=8.8, 6.8, 1.8, Hz, 1H), 7.61 (ddd, J=4.8, 2.8, 2.8 Hz, 2H), 7.58 (s, 1H), 7.24 (ddd, J=5.2, 3.2, 3.2 Hz, 2H), 7.01 (ddd, J=6.8, 5.2, 1.2 Hz, 1H), 6.88 (dd, J=8.4, .4.0 Hz, 1H), 4.64 (t, J=4.2 Hz, 2H), 4.43 (t, J=4.6 Hz, 2H). MS(ES+): m/z 376.47 (10) [MH$^+$].

f) 1-{4-[2-(Pyridin-2-yloxy)ethoxy]phenyl}-1H-benzimidazole-5-carboxylic acid (100 mg, 0.266 mmol) and 1,1'-carbonyldiimidazole (86 mg, 0.53 mmol) were dissolved in dry THF (2 mL) under a N$_2$ atmosphere. The reaction mixture was heated at 60° C. for 1 h and then cooled to rt. Methylamine hydrochloride (27 mg, 0.40 mmol) and N,N'-diisopropylethylamine (52 mg, 0.40 mmol, 70 μL) were added and the reaction was allowed to stir at rt. After 18 h, the reaction mixture was concentrated in vacuo, diluted with CH$_2$Cl$_2$ (2 mL), and washed with distilled water (1 mL). The aqueous phase was back extracted with CH$_2$Cl$_2$ (2 mL×5) and the combined organic extracts were concentrated in vacuo. The resulting yellow solid was purified using the Waters mass-directed HPLC purification system to give N-methyl-1-{4-[2-(pyridin-2-yloxy)ethoxy]phenyl}-1H-benzimidazole-5-carboxamide as a white powder. $^1$H NMR (d$_6$-DMSO, 400 MHz): δ 8.57 (s, 1H), 8.49 (brq, J=4.4 Hz, 1H), 8.28 (d, J=1.2 Hz, 1H), 8.19 (ddd, J=5.2, 2.0, 0.8 Hz, 1H), 7.85 (dd, J=8.6, 1.4 Hz, 1H), 7.74 (ddd, J=8.8, 6.8, 2.0 Hz, 1H), 7.61 (ddd, J=5.2, 3.2, 3.2 Hz, 2H), 7.55 (d, J=9.2 Hz, 1H), 7.23 (ddd, J=5.8, 3.6, 3.6 Hz, 2H), 7.01 (ddd, J=7.2, 5.2, 1.2 Hz, 1H), 6.88 (ddd, J=8.4, 0.8, 0.8 Hz, 1H), 4.63 (m, 2H), 4.43 (m, 2H), 2.82 (d, J=4.8 Hz, 3H). MS(ES+): m/z 389 [MH+].

The following compounds were prepared according to the procedures described above for EXAMPLE N1 utilizing the appropriate amines in place of methylamine hydrochloride.

EXAMPLE N2

N-Ethyl-1-{4-[2-(pyridin-2-yloxy)ethoxy]phenyl}-1H-benzimidazole-5-carboxamide; MS(ES+): m/z 403 [MH+].

EXAMPLE N3

N-(2-Methoxyethyl)-1-{4-[2-(pyridin-2-yloxy)ethoxy]phenyl}-1H-benzimidazole-5-carboxamide; MS(ES+): m/z 433 [MH+].

EXAMPLE N4

N-(2-Morpholin-4-ylethyl)-1-{4-[2-(pyridin-2-yloxy)ethoxy]phenyl}-1H-benzimidazole-5-carboxamide; MS(ES+): m/z 488 [MH+].

EXAMPLE N5

1-{4-[2-(Pyridin-2-yloxy)ethoxy]phenyl}-N-(1-tetrahydro-2H-pyran-4-ylmethyl)-1H-benzimidazole-5-carboxamide; MS(ES+): m/z 473 [MH+].

EXAMPLE N6

1-{4-[2-(Pyridin-2-yloxy)ethoxy]phenyl}-N-tetrahydro-2H-pyran-4-yl-1H-benzimidazole-5-carboxamide; MS(ES+): m/z 459 [MH+].

EXAMPLE N7

N-Cyclobutyl-1-{4-[2-(pyridin-2-yloxy)ethoxy]phenyl}-1H-benzimidazole-5-carboxamide; MS(ES+): m/z 430 [MH+].

EXAMPLE N8

N-(2-Hydroxyethyl)-1-{4-[2-(pyridin-2-yloxy)ethoxy]phenyl}-1H-benzimidazole-5-carboxamide To a 20 mL Bohdan MiniBlock 12-position glass reaction tube, 1-{4-[2-(pyridin-2-yloxy)ethoxy]phenyl}-1H-benzimidazole-5-carboxylic acid (100 mg, 0.27 mmol), PS-HOBt (HL; 269 mg, 0.24 mmol), DMAP (18 mg, 0.15 mmol), CH$_2$Cl$_2$ (1 mL), and DMF (0.25 mL) were added. The reaction mixture was shaken for 5 min. 1,3-Diisopropylcarbodiimide (138 mg, 1.09 mmol) was added to the reaction mixture and shaken for 4 h. The solution was filtered and the resin was washed with CH$_2$Cl$_2$ (3×3 mL), DMF (3×3 mL), and THF (3×3 mL). The resin was resuspended in DMF (1 mL) and 2-aminoethanol (15 mg, 0.24 mmol) and DIEA (31 mg, 0.24 mmol) were added. The reaction mixture was allowed to shake overnight. The reaction mixture was then filtered, and washed with CH$_2$Cl$_2$ (3×3 mL), DMF (3×3 mL), and THF (3×3 mL). The filtrate and the washes were combined and concentrated in vacuo. The crude product was purified by using the Waters mass-directed HPLC purification system to yield N-(2-hydroxyethyl)-1-{4-[2-(pyridin-2-yloxy)ethoxy]phenyl}-1H-benzimidazole-5-carboxamide as a yellowish white powder. $^1$H NMR (d$_6$-DMSO, 400 MHz): δ 8.57 (s, 1H), 8.49 (t, J=4.4 Hz, 1H), 8.32 (d, J=1.2 Hz, 1H), 8.19 (ddd, J=5.2, 2.0, 0.8 Hz, 1H), 7.85 (dd, J=8.4, 1.6 Hz, 1H), 7.74 (ddd, J=9.2, 7.2, 2.0 Hz, 1H), 7.61 (ddd, J=5.6, 3.6, 3.6 Hz, 2H), 7.56 (d, J=8.0 Hz, 1H), 7.23 (ddd, J=6.0, 3.6, 3.6 Hz, 2H), 7.01 (ddd, J=7.2, 5.2, 0.8 Hz, 1H), 6.88 (ddd, J=8.4, 0.8, 0.8 Hz, 1H), 4.63 (m, 2H), 4.43 (m, 2H), 2.82 (d, J=4.8 Hz, 3H). MS(ES+): m/z 419 (60) [MH+].

The following compounds were prepared according to the procedures described above for EXAMPLE N8 utilizing the appropriate amines in place of 2-aminoethanol.

EXAMPLE N9

1-{4-[2-(Pyridin-2-yloxy)ethoxy]phenyl}-N-(2-pyrrolidin-1-ylethyl)-1H-benzimidazole-5-carboxamide; MS(ES+): m/z 472 [MH+].

EXAMPLE N10 tert-Butyl-4-{[(1-{4-[2-(pyridin-2-yloxy)ethoxy]phenyl}-1H-benzimidazol-5-yl)carbonyl]amino}ethyl)piperazine-1-carboxylate; MS(ES+): m/z 587 [MH+].

EXAMPLE N11

N-Isopropyl-1-{4-[2-(pyridin-2-yloxy)ethoxy]phenyl}-1H-benzimidazole-5-carboxamide; MS(ES+): m/z 417 [MH+].

EXAMPLE N12

1-{4-[2-(pyridin-2-yloxy)ethoxy]phenyl}-1H-benzimidazole-5-carboxamide; MS(ES+): m/z 375 [MH+].

The following compounds were prepared according to the procedures described above for EXAMPLE N8 utilizing the appropriate diols and amines in place of ethylene glycol and 2-aminoethanol, respectively.

EXAMPLE N13

1-{4-[1-Methyl-2-(pyridin-2-yloxy)ethoxy]phenyl}-N-(2-morpholin-4-ylethyl)-1H-benzimidazole-5-carboxamide and N-(2-Morpholin-4-ylethyl)-1-{4-[2-(pyridin-2-yloxy)propoxy]phenyl}-1H-benzimidazole-5-carboxamide (1:1 mix of regioisomers); MS(ES+): m/z 503 [MH+].

EXAMPLE N14

N-(2-Morpholin-4-ylethyl)-1-{4-[1-methyl-2-(pyridin-2-yloxy)propoxy]phenyl}-1H-benzimidazole-5-carboxamide; MS(ES+): m/z 517 [MH+].

EXAMPLE N15

1-{4-[1-Methyl-2-(pyridin-2-yloxy)ethoxy]phenyl}-1H-benzimidazole-5-carboxamide and 1-{4-[2-(pyridin-2-yloxy)propoxy]phenyl}-1H-benzimidazole-5-carboxamide (1:1 mix of regioisomers); MS(ES+): m/z 389 [MH+].

EXAMPLE N16

N-Isopropyl-1-{4-[1-methyl-2-(pyridin-2-yloxy)ethoxy]phenyl}-1H-benzimidazole-5-carboxamide and N-Isopropyl-1-{4-[2-(pyridin-2-yloxy)propoxy]phenyl}-1H-benzimidazole-5-carboxamide (1:1 mix of regioisomers); MS(ES+): m/z 431 [MH+].

EXAMPLE N17

N-(2-Hydroxyethyl)-1-{4-[1-methyl-2-(pyridin-2-yloxy)ethoxy]phenyl}-1H-benzimidazole-5-carboxamide and N-(2-Hydroxyethyl)-1-{4-[2-(pyridin-2-yloxy)propoxy]

phenyl}-1H-benzimidazole-5-carboxamide (1:1 mix of regioisomers); MS(ES+): m/z 533 [MH+].

EXAMPLE N18

1-{4-[1-Methyl-2-(pyridin-2-yloxy)ethoxy]phenyl}-N-(2-pyrrolidin-1-ylethyl)-1H-benzimidazole-5-carboxamide and 1-{4-[2-(Pyridin-2-yloxy)propoxy]phenyl}-N-(2-Pyrrolidin-1-ylethyl)-1H-benzimidazole-5-carboxamide (1:1 mix of regioisomers); MS(ES+): m/z 487 [MH+].

EXAMPLE N19

1-{4-[1-Methyl-2-(pyridin-2-yloxy)ethoxy]phenyl}-N-(1-tetrahydro-2H-pyran-4-ylmethyl)-1H-benzimidazole-5-carboxamide and 1-{4-[2-(Pyridin-2-yloxy)propoxy]phenyl}-N-(1-tetrahydro-2H-pyran-4-ylmethyl)-1H-benzimidazole-5-carboxamide (1:1 mix of regioisomers); MS(ES+): m/z 474 [MH+].

EXAMPLE N20

1-{4-[1-Methyl-2-(pyridin-2-yloxy)ethoxy]phenyl}-N-[3-(methylthio)propyl]-1H-benzimidazole-5-carboxamide and N-[3-(Methylthio)propyl]-1-{4-[2-(pyridin-2-yloxy)propoxy]phenyl}-1H-benzimidazole-5-carboxamide (1:1 mix of regioisomers); MS(ES+): m/z 478 [MH+].

EXAMPLE N21

1-{4-[1-methyl-2-(pyridin-2-yloxy)propoxy]phenyl}-1H-benzimidazole-5-carboxamide; MS(ES+): m/z 403 [MH+].

EXAMPLE N22

N-Isopropyl-1-{4-[1-methyl-2-(pyridin-2-yloxy)propoxy]phenyl}-1H-benzimidazole-5-carboxamide; MS(ES+): m/z 446 [MH+].

EXAMPLE N23

N-(2-Hydroxyethyl)-1-{4-[1-methyl-2-(pyridin-2-yloxy)propoxy]phenyl}-1H-benzimidazole-5-carboxamide; MS(ES+): m/z 447 [MH+].

EXAMPLE N24

1-{4-[1-Methyl-2-(pyridin-2-yloxy)propoxy]phenyl}-N-(2-pyrrolidin-1-ylethyl)-1H-benzimidazole-5-carboxamide; MS(ES+): m/z 501 [MH+].

EXAMPLE N25

1-{4-[1-Methyl-2-(pyridin-2-yloxy)propoxy]phenyl}-N-(1-tetrahydro-2H-pyran-4-ylmethyl)-1H-benzimidazole-5-carboxamide; MS(ES+): m/z 488 [MH+].

EXAMPLE N26

1-{4-[1-Methyl-2-(pyridin-2-yloxy)propoxy]phenyl}-N-[3-(methylthio)propyl]-1H-benzimidazole-5-carboxamide; MS(ES+): m/z 492 [MH+].

EXAMPLE N27

N-Methyl-1-{4-[1-methyl-2-(pyridin-2-yloxy)ethoxy]phenyl}-1H-benzimidazole-5-carboxamide and N-Methyl-1-{4-[2-(pyridin-2-yloxy)propoxy]phenyl}-1H-benzimidazole-5-carboxamide (1:1 mix of regioisomers); MS(ES+): m/z 403 [MH+].

EXAMPLE N28

N-Methyl-1-{4-[1-Methyl-2-(pyridin-2-yloxy)propoxy]phenyl}-1H-benzimidazole-5-carboxamide; MS(ES+): m/z 417 [MH+].

EXAMPLE O1

1-(4-{[3-(2-Pyridyloxymethyl)cyclobutyl]oxy}phenyl)-N-pyridin-3-ylmethyl-1H-benzimidazole-5-carboxamide

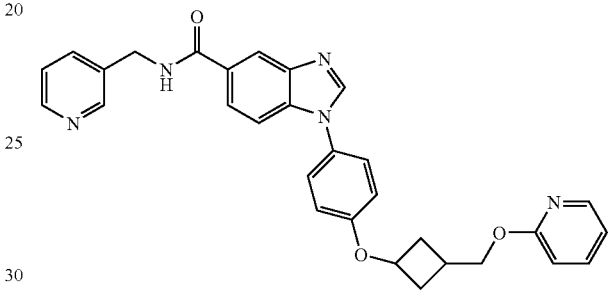

a) Methyl 3-hydroxycyclobutanecarboxylate (671 mg, 5.16 mmol) was dissolved in CH$_2$Cl$_2$ (20 mL). Pyridine (0.63 mL, 7.73 mmol) was then added followed by p-toluenesulfonic anhydride (1.85 g, 5.67 mmol) and the reaction was stirred at rt for 14 h. The reaction was concentrated in vacuo, dissolved in ether, and washed with H$_2$O, 2M HCl, 2M NaHCO$_3$, brine, and dried over MgSO$_4$. The solution was then filtered, and concentrated in vacuo to give methyl 3-{[(4-methylphenyl)sulfonyl]oxy}cyclobutanecarboxylate as a colorless oil, which was taken on crude. 1-(4-Hydroxyphenyl)-N-(pyridin-3-ylmethyl)-1H-benzimidazole-5-carboxamide (0.88 g, 2.56 mmol), 18-crown-6 (1.36 g, 5.13 mmol), and K$_2$CO$_3$ (0.71 g, 5.13 mmol) were dissolved in DMF (26 mL) in a 50 mL round bottom flask. The reaction was heated to 80° C. under N$_2$ atmosphere upon which methyl 3-{[(4-methylphenyl)sulfonyl]oxy}cyclobutanecarboxylate was added drop-wise. After heating at 80° C. for 48 h, the reaction was cooled to rt, concentrated in vacuo, and purified using silica gel chromatography (5% methanol:CH$_2$Cl$_2$). To remove residual p-toluenesulfonic acid and 18-crown-6, the foamy white solid was washed with ethyl acetate. The combined organic washes were then washed with water and dried over MgSO$_4$, filtered, and concentrated in vacuo to provide methyl 3-(4-{5-[(pyridin-3-ylmethylamino)carbonyl]-1H-benzimidazol-1-yl}phenoxy)cyclobutanecarboxylate as an off-white foamy solid (3:1 trans:cis isomers). MS (ES+): m/z 457 (100) [MH+].

Methyl 3-(4-{5-[(pyridin-3-ylmethylamino)carbonyl]-1H-benzimidazol-1-yl}phenoxy)cyclobutanecarboxylate (150 mg, 0.33 mmol) and sodium borohydride (25 mg, 0.66 mmol) were dissolved in THF (3 mL), put under a N$_2$ atmosphere, and heated to 60° C. Methanol (13 μL, 0.33 mmol) was then added and the reaction was stirred at 60° C. for 48 h. The reaction was cooled to rt and concentrated in vacuo. Methanol (2 mL) was then added followed by sodium hydroxide (3M, 5 mL) and the methanol was removed in vacuo. The resultant aqueous solution was extracted with ethyl acetate (3×), dried over MgSO₄, filtered, and concentrated in vacuo. The crude solid was purified using the Waters mass-directed HPLC purification system to provide 1-(4-{[3-(hydroxymethyl)cyclobutyl]oxy}phenyl)-N-pyridin-3-ylmethyl-1H-benzimidazole-5-carboxamide as a white solid. MS (ES+): m/z 429 (90) [MH⁺].

c) 1-(4-{[3-(Hydroxymethyl)cyclobutyl]oxy}phenyl)-N-pyridin-3-ylmethyl-1H-benzimidazole-5-carboxamide (33 mg, 0.08 mmol) was dissolved in DMF and put under N₂ atmosphere. Sodium hydride (2 mg, 0.08 mmol) was added and the reaction was heated to 60° C. 2-Fluoropyridine was then added and the reaction was then heated to 80° C. for 14 h. The reaction was cooled to rt and concentrated in vacuo. The crude solid was purified using the Waters mass-directed HPLC purification system to provide 1-(4-{[3-(2-pyridyloxymethyl)cyclobutyl]oxy}phenyl)-N-pyridin-3-ylmethyl-1H-benzimidazole-5-carboxamide as an off-white solid. MS (ES+): m/z 507 (10) [MH⁺].

EXAMPLE P1

1-{4-[(3-Phenoxypropyl)amino]phenyl}-N-pyridin-3-ylmethyl-1H-benzimidazole-5-carboxamide

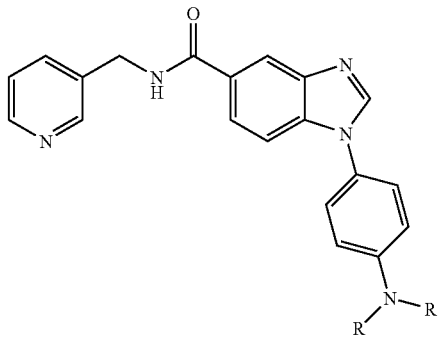

A flask containing 1-(4-bromophenyl)-N-pyridin-3-ylmethyl-1H-benzimidazole-5-carboxamide (EXAMPLE C2, 100 mg, 0.25 mmol) and 3-phenoxypropylamine hydrochloride (54 mg, 0.29 mmol) was evacuated and refilled with N₂ (2×). To this was added BINAP (112 mg, 0.18 mmol), Pd₂dba₃ (55 mg, 0.06 mmol) and t-BuONa (68 mg, 0.7 mmol) in one portion as a mixture, with minimum exposure to air. The flask was again evacuated and refilled with N₂ (3×). Degassed, anhydrous dioxane (2 mL) was added via syringe and the solution was stirred under N₂ for 10 min at rt and then at 80° C. for 18 h. Later, the reaction was cooled to rt, filtered through Celite (using MeOH and CH₂Cl₂ to rinse the Celite), concentrated under reduced pressure and purified using the Waters mass-directed HPLC purification system to provide 1-{4-[(3-phenoxypropyl)amino]phenyl}-N-pyridin-3-ylmethyl-1H-benzimidazole-5-carboxamide as a white solid. MS (ES+): m/z 478 (100) [MH⁺].

The following compounds were prepared according to the procedure described above for EXAMPLE P1 utilizing the appropriate amines in place of 3-phenoxypropylamine and either 1-(3-bromophenyl)-N-pyridin-3-ylmethyl-1H-benzimidazole-5-carboxamide or 1-(4-bromophenyl)-N-pyridin-3-ylmethyl-1H-benzimidazole-5-carboxamide.

EXAMPLE P2

1-{4-[4-(4-Fluorophenyl)piperidin-1-yl]phenyl}-N-pyridin-3-ylmethyl-1H-benzimidazole-5-carboxamide; MS (ES+): m/z 506 (100) [MH⁺].

EXAMPLE P3

1-{4-[4-(4-Fluorophenyl)piperazin-1-yl]phenyl}-N-pyridin-3-ylmethyl-1H-benzimidazole-5-carboxamide; MS (ES+): m/z 507 (100) [MH⁺].

EXAMPLE P4

1-{3-[4-(4-Fluorophenyl)piperidin-1-yl]phenyl}-N-pyridin-3-ylmethyl-1H-benzimidazole-5-carboxamide; MS (ES+): m/z 506 (100) [MH⁺].

EXAMPLE P5

N-Pyridin-3-ylmethyl-1-{3-[(2-thien-3-ylethyl)amino]phenyl}-1H-benzimidazole-5-carboxamide; MS (ES+): m/z 454 (100) [MH⁺].

EXAMPLE P6

1-[3-(Cyclohexylmethylamino)phenyl]-N-pyridin-3-ylmethyl-1H-benzimidazole-5-carboxamide; MS (ES+): m/z 440 (100) [MH⁺].

EXAMPLE P7

1-{4-[(2-Phenoxyethyl)amino]phenyl}-N-pyridin-3-ylmethyl-1H-benzimidazole-5-carboxamide; MS (ES+): m/z 464 (100) [MH⁺].

EXAMPLE P8

1-(3-{[1-(4-Chlorophenyl)ethyl]amino}phenyl)-N-pyridin-3-ylmethyl-1H-benzimidazole-5-carboxamide; MS (ES+): m/z 482 (100) [MH⁺].

EXAMPLE P9

1-(3-{[3-(1H-Imidazol-1-yl)propyl]amino}phenyl)-N-pyridin-3-ylmethyl-1H-benzimidazole-5-carboxamide; MS (ES+): m/z 452 [MH⁺].

EXAMPLE P10

N-Pyridin-3-ylmethyl-1-[3-(4-pyrimidin-2-ylpiperazin-1-yl)phenyl]-1H-benzimidazole-5-carboxamide; MS (ES+): m/z 491 [MH⁺].

EXAMPLE P11

1-(3-[1,4']Bipiperidinyl-1'-yl-phenyl)-N-pyridin-3-ylmethyl-1H-benzimidazole-5-carboxamide; MS (ES+): m/z 495 [MH⁺].

EXAMPLE P12

1-{3-[Benzyl(methyl)amino]phenyl}-N-pyridin-3-ylmethyl-1H-benzimidazole-5-carboxamide; MS (ES+): m/z 448 [MH⁺].

EXAMPLE P13

N-Isopropyl-1-(4-{[4-(trifluoromethoxy)benzyl]amino}phenyl)-1H-benzimidazole-5-carboxamide; MS (ES+): m/z 469 (100) [MH⁺].

EXAMPLE P14

N-Methyl-1-(4-{[4-(trifluoromethoxy)benzyl]amino}phenyl)-1H-benzimidazole-5-carboxamide; MS (ES+): m/z 441 (100) [MH+].

EXAMPLE P15

N-(2-Morpholin-4-ylethyl)-1-(4-{[4-(trifluoromethoxy)benzyl]amino}phenyl)-1H-benzimidazole-5-carboxamide; MS (ES+): m/z 540 (100) [MH+].

EXAMPLE P16

N-Tetrahydro-2H-pyran-4-yl-1-(4-{[4-(trifluoromethoxy)benzyl]amino}phenyl)-1H-benzimidazole-5-carboxamide; MS (ES+): m/z 511 (100) [MH+].

EXAMPLE P17

N-Pyridin-3-ylmethyl-1-(3-{[4-(trifluoromethoxy)benzyl]amino}phenyl)-1H-benzimidazole-5-carboxamide; MS (ES+): m/z 518 (100) [MH+].

EXAMPLE P18

1-{3-[(4-Trifluoromethylphenyl)amino]phenyl}-N-pyridin-3-ylmethyl-1H-benzimidazole-5-carboxamide; MS (ES+): m/z 489 (100) [MH+].

EXAMPLE Q1

1-(3-{[(4-Methylphenyl)sulfonyl]amino}phenyl)-N-pyridin-3-ylmethyl-1H-benzimidazole-5-carboxamide

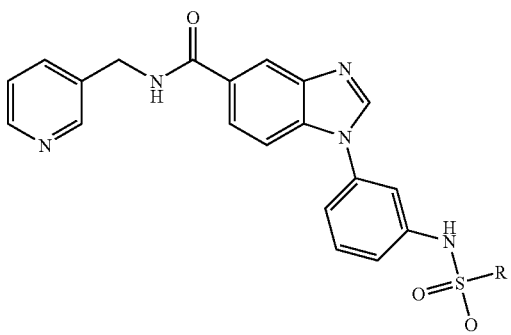

a) A mixture of 4-fluoro-3-nitrobenzoic acid (10.2 g, 54.9 mmol), N-(3-aminophenyl)-acetamide (9.21 g, 66.6 mmol), and Et$_3$N (1.4 mL, 10.1 mmol.) in anhydrous EtOH (160 mL) was heated at reflux under N$_2$ atmosphere. After 16 h, the reaction mixture was cooled and the resultant precipitate filtered. The orange solid was washed with 2 M aq HCl and dried to yield 4-{[3-(acetylamino)phenyl]amino}-3-nitrobenzoic acid. $^1$H NMR (400 MHz, DMSO-d$_6$): δ 2.03 (s, 3H), 7.02 (d, J=7.9 Hz, 1H), 7.13 (d, J=9.0 Hz, 1H), 7.37 (t, J=8.0 Hz, 1H), 7.42 (d, J=8.0 Hz, 1H), 7.68 (s, 1H), 7.93 (dd, J=9.0, 1.9 Hz, 1H), 8.62 (s, 1H), 9.76 (s, 1H), 10.08 (s, 1H), 13.02 (brs, 1H). MS (ES+): m/z 316 [MH+].

A suspension of 4-{[3-(acetylamino)phenyl]amino}-3-nitrobenzoic acid (1.27 g, 4.04 mmol) and iron powder (1.77 g, 31.6 mmol) in HCO$_2$H (30 mL) and HC(OMe)$_3$ (20 mL) was stirred at rt under N$_2$ atmosphere. After 18 h, the reaction mixture was filtered through Celite and the Celite pad was washed with EtOH. The solvent was removed in vacuo. The resultant crude material was purified by silica gel chromatography (10% MeOH in CH$_2$Cl$_2$) to afford 1-[3-(acetylamino)phenyl]-1H-benzimidazole-5-carboxylic acid as a light yellow solid. $^1$H NMR (400 MHz, DMSO-d$_6$): δ 2.07 (s, 3H), 7.36 (d, J=8.4 Hz, 1H), 7.56 (t, J=8.0 Hz, 1H), 7.63 (d, J=8.4 Hz, 1H), 7.69 (d, J=8.8 Hz, 1H), 7.96 (d, J=8.8 Hz, 1H), 8.02 (s, 1H), 8.34 (s, 1H), 8.71 (s, 1H), 10.3 (s, 1H). MS (ES+): m/z 296 [MH+].

c) To a stirred mixture of 1-[3-(acetylamino)phenyl]-1H-benzimidazole-5-carboxylic acid (0.83 g, 2.8 mmol), EDCI (0.81 g, 4.22 mmol), HOBt (0.57 g, 4.22 mmol) in anhydrous DMA (10 mL) was added DIPEA (0.75 mL, 4.31 mmol) at rt. The reaction mixture was stirred for 0.5 h and then (3-aminomethyl)pyridine (0.57 mL, 5.62 mmol) was added dropwise. Stirring was continued for an additional 25 h. The solvent was evaporated in vacuo and the crude material was purified by silica gel chromatography (5%-15% MeOH in CH$_2$Cl$_2$) and then recrystallized from acetone to afford 1-[3-(acetylamino)phenyl]-N-(pyridin-3-ylmethyl)-1H-benzimidazole-5-carboxamide as a light yellow solid. $^1$H NMR (400 MHz, DMSO-d$_6$): δ 2.09 (3H, s), 4.54 (d, J=6.0 Hz, 2H), 7.35-7.40 (m, 2H), 7.56 (t, J=8.0 Hz, 1H), 7.62 (d, J=7.6 Hz, 1H), 7.70 (d, J=8.4 Hz, 1H), 7.76 (d, J=8.4 Hz, 1H), 7.92 (dd, J=8.4 Hz, 1.2 Hz, 1H), 8.04 (t, J=2.0 Hz, 1H), 8.38 (d, J=1.2 Hz, 1H), 8.46 (dd, J=4.8 Hz, 1.6 Hz, 1H), 8.58 (1H, J=1.6 Hz, 1H), 8.68 (s, 1H), 9.21 (t, J=5.6 Hz, 1H), 10.33 (s, 1H). MS (ES+): m/z 386 [MH+].

d) An aqueous HCl (2M, 5 mL) solution of 1-[3-(acetylamino)phenyl]-N-(pyridin-3-ylmethyl)-1H-benzimidazole-5-carboxamide (0.47 g) was heated at reflux. After 40 min, the crude reaction mixture was evaporated under reduced pressure at rt and dried in vacuo to afford 1-(3-aminophenyl)-N-(pyridin-3-ylmethyl)-1H-benzimidazole-5-carboxamide dihydrochloride as a purple solid. $^1$H-NMR (DMSO-d$_6$, 400 MHz): δ 4.00 (brs, 2H), 4.72 (d, J=5.2 Hz, 2H), 7.24 (d, J=7.6 Hz, 1H), 7.39 (d, J=7.6 Hz, 1H), 7.44 (s, 1H), 7.56 (t, J=8.4 Hz, 1H), 7.82 (d, J=8.4 Hz, 1H), 8.10-8.50 (m, 2H), 8.47 (s, 1H), 8.59 (d, J=8.0 Hz, 1H), 8.85 (1H, J=5.6 Hz, 1H), 8.96 (s, 1H), 9.25 (s, 1H), 9.64 (t, J=5.6 Hz, 1H). MS (ES+): m/z 344 [MH+].

e) A mixture of 1-(3-aminophenyl)-N-(pyridin-3-ylmethyl)-1H-benzimidazole-5-carboxamide dihydrochloride (47 mg, 0.14 mmol) and TsCl (27 mg, 0.14 mmol) was dissolved in anhydrous THF (3 mL) at 0° C. and treated with Et$_3$N (95 μL, 0.68 mmol). The reaction mixture was stirred for 72 h and then filtered. The solid residue was washed with THF and the combined washings and filtrate were concentrated in vacuo. The resultant residue was purified by silica gel chromatography (0-7% MeOH in CH$_2$Cl$_2$). Further purification was achieved by trituration with MeOH to afford 1-(3-{[(4-methylphenyl)sulfonyl]amino}phenyl)-N-pyridin-3-ylmethyl-1H-benzimidazole-5-carboxamide as a white solid. $^1$H-NMR (DMSO-d$_6$, 400 MHz): δ 2.35 (s, 3H), 4.54 (d, J=5.6 Hz, 2H), 7.20 (d, J=8.0 Hz, 1H), 7.32-7.44 (m, 4H), 7.50 (t, J=7.6 Hz, 1H), 7.68-7.81 (m, 3H), 7.89 (d, J=8.8 Hz, 1H), 8.36 (s, 1H), 8.47 (brs, 1H), 8.61 (s, 1H), 9.19 (brs, 1H). MS (ES+): m/z 498 [MH+].

The following compounds were prepared according to the procedure described above for EXAMPLE Q1 utilizing the appropriate sulfonyl chlorides in place of TsCl.

EXAMPLE Q2

1-(3-{[(4-Chlorophenyl)sulfonyl]amino}phenyl)-N-pyridin-3-ylmethyl-1H-benzimidazole-5-carboxamide; MS (ES+): m/z 518 (100) [M], 519 (30) [MH+].

EXAMPLE Q3

N-Pyridin-3-ylmethyl-1-{3-[(thien-2-ylsulfonyl)amino] phenyl}-1H-benzimidazole-5-carboxamide 1-(3-Aminophenyl)-N-(pyridin-3-ylmethyl)-1H-benzimidazole-5-carboxamide dihydrochloride (60 mg, 0.17 mmol) was dissolved in 2 mL pyridine at 0° C. and 2-thiophenesulphonyl chloride (31 mg, 0.17 mmol) was added in one portion to the mixture, and the reaction was stirred room temperature. After 16 h, the reaction mixture was concentrated in vacuo. The residue was purified using the Waters mass-directed HPLC purification system to yield N-pyridin-3-ylmethyl-1-{3-[(thien-2-ylsulfonyl)amino]phenyl}-1H-benzimidazole-5-carboxamide as a white solid. $^1$H NMR (400 MHz, CD$_3$OD): δ 8.60 (s, 1H), 8.48 (d, J=12.0 Hz, 2H), 8.30 (s, 1H), 7.90 (t, J=8.0 Hz, 2H), 7.69 (d, J=4.0 Hz, 1H), 7.55 (dd, J=1.2 Hz, 4.0 Hz, 1H), 7.48-7.43 (m, 3H), 7.37 (t, J=2.0 Hz, 1H), 7.21 (t, J=8.0 Hz, 1H), 7.09 (t, J=8.0 Hz, 1H), 4.67 (d, J=5.4 Hz, 2H). MS (ES+): m/z 490 [MH$^+$].

The following compounds were prepared according to the procedure described above for EXAMPLE Q3 utilizing the appropriate sulfonyl chlorides in place of thiophenesulphonyl chloride.

EXAMPLE Q4

N-Pyridin-3-ylmethyl-1-[3-({[4-(trifluoromethoxy)phenyl]sulfonyl}amino)phenyl]-1H-benzimidazole-5-carboxamide; MS (ES+): m/z 490 [MH$^+$].

Compound Q5

1-(3-{[(3-Chlorophenyl)sulfonyl]amino}phenyl)-N-pyridin-3-ylmethyl-1H-benzimidazole-5-carboxamide; MS (ES+): m/z 519 [MH$^+$]. This compound displayed results greater than 10 μM in the assay above.

EXAMPLE Q6

1-(3-{[(2,4-Difluorophenyl)sulfonyl]amino}phenyl)-N-pyridin-3-ylmethyl-1H-benzimidazole-5-carboxamide; MS (ES+): m/z 520 [MH$^+$].

EXAMPLE Q7

1-(3-{[(3,4-Dichlorophenyl)sulfonyl]amino}phenyl)-N-pyridin-3-ylmethyl-1H-benzimidazole-5-carboxamide; MS (ES+): m/z 553 [MH$^+$].

What is claimed is:
1. A compound represented by Formula (I):

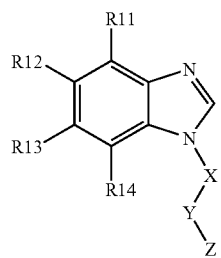

(I)

wherein:
one of R11, R12, R13 and R14 is —NR$_3$COR$_{31}$, —NR$_3$CONR$_3$R$_{31}$, —NR$_3$SO$_2$R$_{31}$, —CO$_2$R$_3$, —CO$_2$H, —C$_{0-8}$alkylNR$_3$R$_{31}$ or —CONR$_3$R$_3$R$_{31}$; and the others are each independently F, Cl, Co$_{0-3}$alkyl, C$_{0-8}$alkoxy, or —N(C$_{0-8}$alkyl)(C$_{0-8}$alkyl);

X is phenyl, optionaily substituted with 1-4 of halogen, —NR$_{32}$R$_{33}$, —NR$_{32}$COR$_{33}$, —NR$_{32}$CO2R$_{33}$, —NR$_{32}$SO$_2$R$_{33}$, —OR$_{32}$, SR$_{32}$, —SO$_2$R$_{32}$, —SO$_2$NR$_{32}$R$_{33}$, —CO$_2$R$_{32}$, —CO$_2$H, —CONR$_{32}$R$_{33}$, —C$_{0-8}$alkyl, —C$_{2-8}$alkenyl, —C$_{2-8}$alkynyl, —CN, CF$_3$, OCF$_3$, NO$_2$, or oxo;

Y is

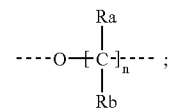

wherein the point of attachment to X can be from either the left or the right as shown;
R$_a$ and R$_b$, are each independently C$_{0-8}$alkyl or C$_{3-8}$cycloallcyl; or R$_a$ and R$_b$, taken together with the C to which they are attached form a saturated or partially unsaturated 3-10 membered ring;
n is 1, 2, 3, 4 or 5;
Z is phenyl, optionally substituted with 1-5 independent halogen, —NR$_{34}$R$_{35}$, —NR$_{34}$COR$_{35}$, —NR$_{34}$C(O) OR$_{35}$, —NR$_{34}$SO$_2$R$_{35}$, —OR$_{34}$, —SR$_{34}$, —SO$_2$R$_{34}$, —SO$_2$NR$_{34}$R$_{35}$, —C(O)OR$_{34}$, —CO$_2$H, —CONR$_{34}$R$_{35}$, C$_{0-8}$alkyl, C$_{2-8}$alkenyl, C$_{2-8}$alkynyl, —OC$_{0-8}$alkyl, —SC$_{0-8}$alkyl, —SO$_2$C$_{0-8}$alkyl, —SO$_2$N (C$_{0-8}$alkyl)(C$_{0-8}$alkyl), —C(O)OC$_{0-8}$alkyl, CN, CF$_3$, NO$_2$, oxo, carbocyclyl, C$_{0-8}$alkyl-O—C$_{0-8}$alkyl, C$_{0-8}$alkyl-O—C(O)—C$_{0-8}$alkyl, or C$_{0-8}$alkyl-C(O)-O—C$_{0-8}$alkyl;
R$_3$, R$_{34}$, and R$_{35}$ are independently —CF$_3$, —CHF$_2$, —C$_{0-8}$ alkyl-O—C$_{0-8}$alkyl, —C$_{0-8}$alkyl-N(C$_{0-8}$alkyl) (C$_{0-8}$ alkyl), —C$_{0-8}$alkyl-S(O)$_{0-2}$—C$_{0-8}$alkyl, —C$_{0-8}$ alkyl-S(O)$_2$N(C$_{0-8}$alkyl)(C$_{0-8}$alkyl), or C$_{0-8}$alkyl optionally substituted with OH;
R$_{31}$ is C$_{0-8}$alkyl substituted by morpholinyl;
R$_{32}$ and R$_{33}$ are independently —CF$_3$, —CHF$_2$, —C$_{0-8}$ alkyl-O—C$_{0-8}$alkyl, C$_{0-8}$alkyl-N(C$_{0-8}$alkyl)(C$_{0-8}$ alkyl), C$_{0-8}$alkyl-S(O)$_{0-2}$—C$_{0-8}$alkyl, or —C$_{0-8}$alkyl-S(O)$_2$N (C$_{0-8}$alkyl)(C$_{0-8}$alkyl);
provided that when Y is —OCH$_2$—, Z must be substituted with 1-5 —NR$_{34}$R$_{35}$, —NR$_{34}$COR$_{35}$, —NR$_{34}$C(O) OR$_{35}$, —NR$_{34}$SO$_2$R$_{35}$, —OR$_{34}$, —SR$_{34}$, —SO$_2$R$_{34}$, —SO$_2$NR$_{34}$R$_{35}$, —CO$_2$R$_{34}$, —CO$_2$H, —CONR$_{34}$ R$_{35}$, C$_{0-8}$alkyl, C$_{2-8}$alkenyl, C$_{2-8}$alkynyl, CF$_3$, NO$_2$, oxo, or carbocyclyl substituents optionally substituted with OH;
or a pharmaceutically acceptable salt or N-oxide thereof.

2. A compound represented by Formula (I):

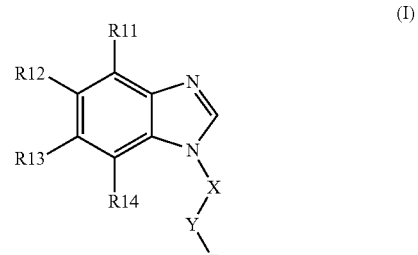

(I)

wherein:
R11, R13, and R14 are independently F, Cl, $C_{0-3}$alkyl, $C_{0-8}$alkoxy, or —N($C_{0-8}$alkyl)($C_{0-8}$alkyl);
R12 is —$NR_3COR_{31}$, —$NR_3CONR_3R_{31}$, —$NR_3SO_2R_{31}$, —$CO_2R_3$, —$CO_2H$, —$C_{0-8}$alkyl$NR_3R_{31}$, or —$CONR_3R_{31}$;
X is phenyl, optionally substituted with 1-4 of halogen, —$NR_{32}R_{33}$, —$N_{32}COR_{33}$, —$NR_{32}CO2R_{33}$, —$NR_{32}SO_2R_{33}$, —$OR_{32}$, —$SR_{32}$, —$SO_2R_{32}$, —$SO_2NR_{32}R_{33}$, —$CO_2R_{32}$, —$CO_2H$, —$CONR_{32}R_{33}$, —$C_{0-8}$alkyl, —$C_{2-8}$alkenyl, —$C_{2-8}$alkynyl, —CN, $CF_3$, $OCF_3$, $NO_2$, or oxo;
Y is

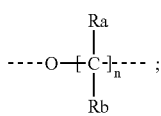

wherein the point of attachment to X can be from either the left or the right as shown;
$R_a$ and $R_b$ are each independently $C_{0-8}$alkyl or $C_{3-8}$cycloalkyl; or $R_a$ and $R_b$ taken together with the C to which they are attached form a saturated or partially unsaturated 3-10 membered ring;
n is 1, 2, 3, 4 or 5;
Z is phenyl, optionally substituted with 1-5 independent halogen, —$NR_{34}R_{35}$, —$NR_{34}COR_{35}$, —$NR_{34}C(O)OR_{35}$, —$NR_{34}SO_2R_{35}$, —$OR_{34}$, —$SR_{34}$, —$SO_2R_{34}$, —$SO_2NR_{34}R_{35}$, —$C(O)OR_{34}$, —$CO_2H$, —$CONR_{34}R_{35}$, $C_{0-8}$alkyl, $C_{2-8}$alkenyl, $C_{2-8}$alkynyl, —$OC_{0-8}$alkyl, —$SC_{0-8}$alkyl, —$SO_2C_{0-8}$alkyl, —$SO_2N(C_{0-8}$alkyl)($C_{0-8}$alkyl), —$C(O)OC_{0-8}$alkyl, CN, $CF_3$, $NO_2$, oxo, carbocyclyl, $C_{0-8}$alkyl-O—$C_{0-8}$alkyl, $C_{0-8}$alkyl-O—C(O)—$C_{0-8}$alkyl, or $C_{0-8}$alkyl-C(O)-O—$C_{0-8}$alkyl;
$R_3$, $R_{34}$, and $R_{35}$ are independently —$CF_3$, —$CHF_2$, —$C_{0-8}$ alkyl-O—$C_{0-8}$alkyl, —$C_{0-8}$alkyl-N($C_{0-8}$alkyl)($C_{0-8}$ alkyl), —$C_{0-8}$alkyl-S(O)$_{0-2}$—$C_{0-8}$alkyl, —$C_{0-8}$ alkyl-S(O)$_2$N($C_{0-8}$alkyl)($C_{0-8}$alkyl), or $C_{0-8}$alkyl optionally substituted with OH;
$R_{31}$ is $C_{0-8}$alkyl substituted by morpholinyl;
$R_{32}$ and $R_{33}$ are independently —$CF_3$, —$CHF_2$, —$C_{0-8}$ alkyl-O—$C_{0-8}$alkyl-N($C_{0-8}$alkyl)($C_{0-8}$alkyl), —$C_{0-8}$ alkyl-S(O)$_{0-2}$—$C_{0-8}$alkyl, or —$C_{0-8}$alkyl-S(O)$_2$N($C_{0-8}$ alkyl)($C_{0-8}$alkyl);
provided that when Y is —$OCH_2$, Z must be substituted with 1-5 —$NR_{34}R_{35}$, —$NR_{34}COR_{35}$, —$NR_{34}C(O)$ $OR_{35}$, —$NR_{34}SO_2R_{35}$, —$OR_{34}$, —$SR_{34}$, —$SO_2R_{34}$, —$SO_2NR_{34}R_{35}$, —$CO_2R_{34}$, —$CO_2H$, —$CONR_{34}R_{35}$, $C_{0-8}$alkyl, $C_{2-8}$alkenyl, $C_{2-8}$alkynyl, $CF_3$, $NO_2$, oxo, or carbocyclyl substituents;
or a pharmaceutically acceptable salt or N-oxide thereof.

3. The compound, salt, or N-oxide of claim 2, wherein R12 is —$CONR_3R_{31}$.

4. A pharmaceutical composition comprising the compound, salt, or N-oxide of claim 1 and a pharmaceutically acceptable carrier.

5. A compound selected from:
N-(2-morpholin-4-ylethyl)-1-(4-{[4-(trifluoromethoxy) benzyl]oxy}phenyl)-1H -benzimidazole-5-carboxamide;
N-(3-morpholin-4-ylpropyl)-1-(4-{[4-(trifluoromethoxy) benzyl]oxy}phenyl)-1H -benzimildazole-5-carboxamide;
or a pharmaceutically acceptable salt or N-oxide thereof.

6. A compound selected from:
1-{4-[3-(4-fluorophenoxy)propoxy]phenyl}-N-(3-morpholin-4ylpropyl)-1H -benzimidazole-5-carboxamide;
1-{4-[3-(4-fluorophenoxy)propoxy]phenyl}-N-(2-morpholin-4ylethyl)-1H -benzimidazole-5-carboxamide;
N-(2-morpholin-4-ylethyl)-1-(3-{[4-(trifluoromethoxy) benzyl]oxy }phenyl)-1H -benzimidazole-5-carboxamide;
N-(3-morpholin-4-ylpropyl)-1(3-{[4-(trifluoromethoxy) benzyl]oxy}phenyl)-1H -benzimidazole-5-carboxamide;
5-(morpholin-4-ylcarbonyl)-1-(3{[4-(trifluoromethoxy) benzyl]oxy}phenyl)-1H -benzimidazole;
1-{3-[3-(4-fluorophenoxy)propoxy]phenyl}-N-(3-morpholin-4ylpropyl)-1H -benzimidazole-5-carboxamide;
N-(2-morpholin-4ylethyl)-1-[4-({4-[(trifluoromethyl) thio]benzyl}oxy)pheny]1H -benzimidazole-5-carboxamide;
N-(2-morpholin-4yletyl)-1-(4-{[4-(trifluoromethoxy) benzyl]oxy}phenyl)-1H -benzimidazole-5-carboxamide;
N-(2-morpholin-4ylethyl)-1-(4-{[4-(difluoromethoxy) benzyl]oxy}phenyl)1H -benzimidazole-5-carboxamide;
N-(2-morpholin-4ylethyl)-1-(4-{[4-(trifluoromethoxy) benzyl]amino}phenyl)-1H -benzimidazole-5-carboxamide;
or a pharmaceutically acceptable salt or N-oxide thereof.

* * * * *

UNITED STATES PATENT AND TRADEMARK OFFICE
CERTIFICATE OF CORRECTION

| | | |
|---|---|---|
| PATENT NO. | : 7,521,448 B2 | |
| APPLICATION NO. | : 10/921414 | |
| DATED | : April 21, 2009 | |
| INVENTOR(S) | : Bolger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 959 days.

Signed and Sealed this
Eighth Day of March, 2011

David J. Kappos
*Director of the United States Patent and Trademark Office*